US008138350B2

(12) United States Patent
Jeschke et al.

(10) Patent No.: US 8,138,350 B2
(45) Date of Patent: Mar. 20, 2012

(54) N'-CYANO-N-HALOGENALKYLIMIDAMIDE DERIVATIVES

(75) Inventors: Peter Jeschke, Bergisch Gladbach (DE); Robert Velten, Langenfeld (DE); Rüdiger Fischer, Pulheim (DE); Achim Hense, Leverkusen (DE); Michael Edmund Beck, Monheim (DE); Olga Malsam, Rösrath (DE); Udo Reckmann, Köln (DE); Ralf Nauen, Langenfeld (DE); Ulrich Görgens, Ratingen (DE); Leonardo Pitta, Leverkusen (DE); Erich Sanwald, Kiel (DE); Christian Arnold, Langenfeld (DE)

(73) Assignee: Bayer Cropscience AG (DE)

( * ) Notice: Subject to any disclaimer, the term of this patent is extended or adjusted under 35 U.S.C. 154(b) by 0 days.

(21) Appl. No.: 12/374,231

(22) PCT Filed: Jul. 7, 2007

(86) PCT No.: PCT/EP2007/006044
§ 371 (c)(1),
(2), (4) Date: Oct. 29, 2009

(87) PCT Pub. No.: WO2008/009360
PCT Pub. Date: Jan. 24, 2008

(65) Prior Publication Data
US 2010/0048646 A1  Feb. 25, 2010

(30) Foreign Application Priority Data

Jul. 20, 2006 (DE) .......................... 10 2006 033 572

(51) Int. Cl.
A61K 31/44 (2006.01)
C07D 213/00 (2006.01)
(52) U.S. Cl. ....................... 546/332; 514/357
(58) Field of Classification Search ............... 546/330; 514/357
See application file for complete search history.

(56) References Cited

U.S. PATENT DOCUMENTS

| 4,030,994 A | 6/1977 | Kollonitsch |
| 4,587,337 A | 5/1986 | Weiss et al. |
| 4,670,559 A | 6/1987 | Szczepanski |
| 4,734,413 A | 3/1988 | Wade |
| 4,748,243 A | 5/1988 | Beck et al. |
| 4,778,896 A | 10/1988 | Gallenkamp |
| 4,990,622 A | 2/1991 | Jelich |
| 5,116,993 A | 5/1992 | Jelich |
| 5,163,996 A | 11/1992 | Meyer |
| 5,364,989 A * | 11/1994 | Aoki et al. ............ 568/946 |
| 5,420,270 A | 5/1995 | Chandrakumar et al. |
| 5,422,035 A | 6/1995 | Bartmann et al. |
| 5,612,358 A * | 3/1997 | Ishimitsu et al. ........ 514/357 |
| 5,679,796 A | 10/1997 | Kraatz |
| 5,708,180 A | 1/1998 | Beck et al. |
| 5,977,148 A * | 11/1999 | Matsuda et al. .......... 514/357 |
| 6,022,974 A | 2/2000 | Werbitzky et al. |
| 6,114,363 A | 9/2000 | Oberdorf et al. |
| 2006/0035978 A1 | 2/2006 | Hense et al. |

FOREIGN PATENT DOCUMENTS

| DE | 34 11 203 C1 | 6/1985 |
| DE | 36 30 046 A1 | 3/1988 |
| DE | 36 31 538 A1 | 3/1988 |
| DE | 43 15 371 A1 | 11/1994 |
| DE | 44 29 465 A1 | 2/1996 |
| EP | 0 284 174 A1 | 9/1988 |
| EP | 0 302 389 A2 | 2/1989 |
| EP | 0 373 464 A2 | 6/1990 |
| EP | 0 393 453 A2 | 10/1990 |
| EP | 0 420 815 A1 | 4/1991 |
| EP | 0 446 913 A1 | 9/1991 |
| EP | 0 569 947 A1 | 11/1993 |
| EP | 0 775 700 A1 | 5/1997 |
| EP | 0 780 384 A2 | 6/1997 |
| EP | 0 794 180 A1 | 9/1997 |
| JP | 5-239034 A | 9/1993 |
| WO | WO 91/04965 A1 | 4/1991 |
| WO | WO 93/00341 A1 | 1/1993 |
| WO | WO 97/00265 A1 | 1/1997 |
| WO | WO 97/10226 A1 | 3/1997 |
| WO | WO 97/30032 A1 | 8/1997 |
| WO | WO 98/33772 A1 | 8/1998 |
| WO | WO 99/29694 A1 | 6/1999 |
| WO | WO 00/46196 A1 | 8/2000 |
| WO | WO 02/44145 A1 | 6/2002 |
| WO | WO 03/095418 A1 | 11/2003 |
| WO | WO 2004/082616 A2 | 9/2004 |

OTHER PUBLICATIONS

Hcaplus 1999:704997, "Amine termiticides", USPN 5977148, Matsuda et. al., 1999.*
Hcaplus 2003:341680, "Insecticidal and neuroblocking activities of acetamiprid and related compounds", Kiriyama et. al., 2003.*
Patani, G. et al., Chem. Rev. 1996, vol. 96, pp. 3147-3176.*
Allen, C.F.H. and Thirtle, J.R., "2-Bromopyridine [Pyridine, 2-bromo-]," *Org. Synth. Coll.* 3:136 and 26:16, CambridgeSoft Corporation, Cambridge, MA USA (1955 and 1946).
Arnold, B. and Regitz, M., "N-Cyano-α-Diazoimine-Synthese Und Umlagerung Zu N-Cyanoketeniminen," *Tetrahedron Letts.* 21:909-912, Pergamon Press Ltd., Great Britain, UK (1980).
Boyer, J.H. and Schoen, W., "2,3-ψ-Dinitrosopyridines," *J. Am. Chem. Soc.* 78:423-425, American Chemical Society, Washington, DC USA (1956).
Cabanal-Duvillard, I. and Berrien, J.-F., "A Simple Access to Key Pyridine Building Blocks," *Heterocycl. Commun.* 5:257-262, Freund Publishing House Ltd., Israel (1999).

(Continued)

*Primary Examiner* — Janet Andres
*Assistant Examiner* — Heidi Reese
(74) *Attorney, Agent, or Firm* — Sterne, Kessler, Goldstein & Fox PLLC

(57) ABSTRACT

The present application relates to novel substituted N'-cyano-N-halogenalkylimidamide derivatives, to processes for their preparation and to their use for controlling animal pests, especially arthropods, in particular insects.

8 Claims, No Drawings

OTHER PUBLICATIONS

Cottet, F., et al., "Further Metalations and Functionalizations of Chloro-, Bromo- and Iodo(trifluoromethyl)pyridines," *Synthesis* 10:1619-1624, Georg Thieme Verlag Stuttgart, Germany (2004).

Crossland, R.K. and Servis, K.L., "A Facile Synthesis of Methanesulfonate Esters," *J. Org. Chem.* 35:3195-3196, American Chemical Society, Washington, DC USA (1970).

Donetti, A., et al., "N-(Fluoroethyl)(imidazolylphenyl)formamidines. The Issue of the Active Species of Mifentidine," *J. Med. Chem.* 32:957-961, American Chemical Society, Washington, DC USA (1989).

Eiermann, U., et al., "[2.2](2,5)Pyrimidinophanes: Synthesis and Molecular Structure," *Chem. Ber.* 123:1885-1889, Wiley-VCH Verlagsgesellschaft GmbH, Weinheim, Germany (1990).

Graf, V.D., "Die Rosenmundsche Aldehydsynthese in der Pyridinreihe," *Journal für Praktische Chemie* 134:177-187, Verlag GmbH & Co. KGaA, Weinheim, Germany (1932).

Jeschke, P., "The Unique Role of Fluorine in the Design of Active Ingredients for Modern Crop Protection," *ChemBioChem* 5:571-589, Wiley-VCH Verlag GmbH, Weinheim, Germany (2004).

Kababu, S., et al., "5-Azidoimidacloprid and an Acyclic Analogue as Candidate Photoaffinity Probes for Mammalian and Insect Nicotinic Acetylcholine Receptors," *J. Med. Chem.* 43:5003-5009, American Chemical Society, Washington, DC USA (2000).

Kagabu, S., et al., "Effects of Halogen Introduction at the C5 Position of the Imidacloprid Pyridine Ring upon Insecticidal Activity," *J. Pestic Sci.* 30:409-413, Pesticide Science Society of Japan, Tokyo, Japan (Aug. 2005).

Kamal, A., et al., "Facile and efficient synthesis of fluoroalkyl aryl ethers," *Tetrahedron Lett.* 43:7353-7355, Elsevier Science Ltd., Amsterdam, The Netherlands (2002).

Lwowski, W., "Convenient Preparation of Alkyl N-Cyanomidates," *Synthesis* 5:263, Georg Thieme Verlag Stuttgart, Germany (1971).

Marvel, C.S. and Sekera, V.C., "*n*-Dodecyl (Lauryl) *p*-Toluenesulfonate," *Org. Synth. Coll.* 3:366-367, CambridgeSoft Corporation, Cambridge, MA USA (1955).

Möller, F. and Schröter, Methoden der Organischen Chemie (Houben-Weyl), vol. XI/1, p. 602, George Themie Verlag, Stuttgart, Germany (1957).

Möller, F. and Schröter, R., Methoden der Organischen Chemie (Houben-Weyl), vol. XI/1, p. 648, George Themie Verlag, Stuttgart, Germany (1960).

Moore, M.L., "Chapter 7: The Leuckart Reaction," *Organic Reactions*, vol. 5, pp. 301-330, John Wiley & Sons, Inc., New York, NY USA (1949).

Pérez, M.A., et al., "A Simple, Unambiguous Synthesis of 2-Amino-4-oxo- and -4-thioxo-3,4-dihydropyrimidine-5-carbonitriles," *Synthesis* 5:402-404, Georg Thieme Verlag Stuttgart, Germany (1983).

Pesti, J.A., et al., "Efficient Pyridinylmethyl Functionalization: Synthesis of 10,10-Bis[(2-fluoro-4-pyridinyl)methyl]-9(10$H$)-anthracenone (DMP 543), an Acetylcholine Release Enhancing Agent," *J. Org. Chem.* 65:7718-7722, American Chemical Society, Washington, DC USA (2000).

Pevarello, P. and Varasi, M., "An Improved Synthesis of Muscimol," *Synth. Commun.* 22:1939-1948, Marcel Dekker, Inc., New York, NY USA (1992).

Roedig, A., Methoden der Oganischen Chemie (Houben-Weyl), vol. V/4, pp. 13, George Themie Verlag, Stuttgart, Germany (1957).

Roos, A.T., et al., "*n*-Butyl *p*-Toluenesulfonate (*p*-Toluenesulfonic acid, butyl ester)," *Org. Synth. Coll.* 1:145-147, CambridgeSoft Corporation, Cambridge, MA USA (1941).

Sato, N., "Studies of Pyrazines. 13[1] Chlorination of 1-Hydroxy-2(1$H$)-pyrazinones with Phosphoryl Chloride. Formation of 2,5-Dichloro-3-phenylpyrazine from 1-Hydroxy-3-phenyl-2(1$H$)-pyrazinone," *J. Heterocyclic Chem.* 23:149-151, Journal of Heterocyclic Chemistry, Provo, UT USA (1986).

Schäfer, V.H. and Gewald, K., "Einstufige Synthese von Arylaminomethylen-cyanamiden," *Journal für Praktische Chemie* 318:347-349, Wiley, Verlag GmbH & Co. KGaA, Weinheim, Germany (1976).

Setliff, F.L., "Some 2,5- and 5,6-Dihalonicotinic Acids and Their Precursors," *J. Chem. Eng. Data* 15:590-591, American Chemical Society, Washington, DC USA (1970).

Setliff, F.L. and Hule, W.R., "Some Methyl 2,5- and 5,6-Dihalonicotinates," *J. Chem. Eng. Data* 26:332-333, American Chemical Society, Washington, DC USA (1981).

Setliff, F.L., "The Synthesis of Two New 2,3-Dihalo-5-Methylpyridines," *Org. Preparations and Preparations Int.* 3:217-222, Organic Preparations and Procedures, Inc., Newton Highlands, MA USA (1971).

Setliff, F.L. and Rankin, G.O., "Some 2,5- and 5,6-Dihalonicotinic Acids and Their Precursors. II," *J. Chem. Eng. Data* 17:515-516, American Chemical Society, Washington, DC USA (1972).

Setliff, F.L. and Greene, J.S., "Some 2,5- and 5,6-Dihalonicotinic Acids and Their Precursors. 5," *J. Chem. Eng. Data* 23:96-97, American Chemical Society, Washington, DC USA (1978).

Setliff, F.L. and Lane, J.E., "Some 2,5- and 5,6-Dihalonicotinic Acids and Their Precursors. IV," *J. Chem. Eng. Data* 21:246-247, American Chemical Society, Washington, DC USA (1976).

Setliff, F.L. and Price, D.W., "Some 2,5- and 5,6-Dihalonicotinic Acids and Their Precursors. III," *J. Chem. Eng. Data* 18:449-450, American Chemical Society, Washington, DC USA (1973).

Tomizawa, M. and Casida, J.E., "Neonicotinoid Insecticide Toxicology: Mechanisms of Selective Action," *Annu. Rev. Pharmacol. Toxicol.* 45:247-268, Annual Reviews, Palo Alto, CA USA (2005).

Yamada, T., et al., "7 A Novel Insecticide, Acetamiprid," in *Nicotinoid Insecticides and Nicotinic Acetylcholine Receptor*, 1st ed., Izuru Yamamoto, John E. Casida eds., Tokyo; Berlin; Heidelberg; New York: Springer, pp. 149-176 (1999).

English Abstract of Japanese Patent JP 5-239034 A (listed as document FP12 on accompanying form PTO/SB/08A).

International Search Report for International Application No. PCT/EP2007/006044, European Patent Office, Netherlands, mailed on Jan. 17, 2008.

English translation of Written Opinion for International Application No. PCT/EP2007/006044, European Patent Office, Netherlands, dated Feb. 12, 2009.

\* cited by examiner

N'-CYANO-N-HALOGENALKYLIMIDAMIDE DERIVATIVES

This application is a National Stage of International Application No. PCT/EP2007/006044, filed Jul. 7, 2007, which claims the benefit of German Patent Application No. 10 2006 033 572.4, filed Jul. 20, 2006.

The present application relates to novel substituted N'-cyano-N-halogenalkylimidamide derivatives, to processes for their preparation and to their use for controlling animal pests, especially arthropods, in particular insects.

Certain N'-cyano-N-alkylimidamide derivatives are already known as pesticides (cf. WO 03/095418 A1). In addition, certain N'-cyano-N-monohalomethylimidamide derivatives have been described as pesticides (cf. WO 91/04965 A1, T. Yamada, H. Takahashi, R. Hatano, In: Yamamoto I., Casida J. E. (Eds.), *Neonicotinoid Insecticides and Nicotinic Acetylcholine Receptor*, New York, pp. 149-175; P. Jeschke *Chem Bio Chem* 5, 570-589, 2004).

Modern crop protection agents have to satisfy many demands, for example with respect to efficacy, persistence and spectrum of their action and possible use. Questions of toxicity, the combinability with other active compounds or formulation auxiliaries play a role, as well as the question of the expense that the synthesis of an active compound requires. Furthermore, resistances may occur. For all these reasons, the search for novel crop protection agents cannot be considered as having been concluded, and there is a constant need for novel compounds having properties which, compared to the known compounds, are improved at least in respect of individual aspects.

This invention now provides novel compounds of the formula (I)

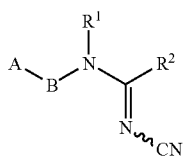

(I)

in which
A represents in each case optionally substituted aryl, heterocyclyl or hetaryl which are optionally substituted by fluorine, chlorine, bromine, iodine, cyano, nitro, alkyl (which is optionally substituted by fluorine and/or chlorine), alkylthio (which is optionally substituted by fluorine and/or chlorine) or alkylsulphonyl (which is optionally substituted by fluorine and/or chlorine),
$R^1$ represents in each case halogen-substituted $C_2$-$C_4$-alkyl, $C_2$-$C_5$-alkenyl or $C_3$-$C_5$-cycloalkyl,
$R^2$ represents in each case optionally halogen-substituted alkyl or cycloalkyl,
B represents optionally substituted methylene or in each case optionally substituted alkylene or alkylidene having in each case 2 to 6 carbon atoms, or denotes a bond between A and $NR^1$.

Furthermore, it has been found that the compounds of the formula (I) according to the invention are obtained when
a) according to preparation method 1, compounds of the formula (II)

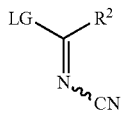

(II)

in which
$R^2$ is as defined above and LG represents a suitable leaving group, for example $C_1$-$C_2$-alkoxy are,
in a first reaction step, reacted with compounds of the formula (III)

(III)

in which
$R^1$ is as defined above,
if appropriate in the presence of a suitable diluent and if appropriate in the presence of a basic auxiliary, to give compounds of the formula (IV)

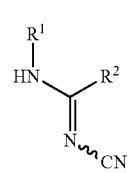

(IV)

in which
$R^1$ and $R^2$ are as defined above,
and these are then, in a second reaction step, reacted with compounds of the formula (V)

(V)

in which
A and B are as defined above,
E represents a suitable leaving group LG, such as, for example, halogen (in particular bromine, chlorine, iodine) O-sulphonylalkyl or o-sulphonylaryl (in particular O-mesyl, O-tosyl),
if appropriate in the presence of a suitable diluent and if appropriate in the presence of a basic auxiliary or
b) according to preparation method 2, compounds of the formula (II)

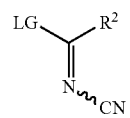

(II)

in which
$R^2$ and LG are as defined above
are reacted with compounds of the formula (VI)

(VI)

in which
A, B and $R^1$ are as defined above,
if appropriate in the presence of a suitable diluent and if appropriate in the presence of a basic auxiliary, or
c) according to preparation method 3, orthoesters of the formula (VII)

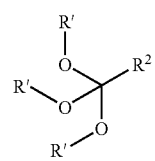

(VII)

in which
$R^2$ is as defined above and
R' represents methyl or ethyl are, in a first reaction step, reacted in situ with cyanamide, if appropriate in the presence of diluents, to give compounds of the formula (II)

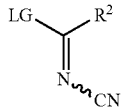
(II)

in which
R² and LG are as defined above,
and these are then, in a second reaction step, reacted with compounds of the formula (VIII)

A-B—NH₂   (VIII)

in which
A and B are as defined above,
if appropriate in the presence of a suitable diluent and if appropriate in the presence of a basic auxiliary, to give compounds of the formula (IX)

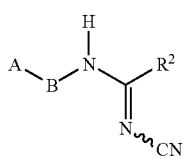
(IX)

in which
A, B, R² are as defined above,
and these are then, in a third reaction step, reacted with compounds of the formula (X)

R¹-E   (X)

in which
R¹ and E are as defined above,
if appropriate in the presence of a suitable diluent and if appropriate in the presence of a basic auxiliary.

Finally, it has been found that novel compounds of the formula (I) have pronounced biological properties and are suitable especially for controlling animal pests, in particular insects, arachnids and nematodes, encountered in agriculture, in forests, in the protection of stored products and materials and in the hygiene sector.

If appropriate, the compounds of the formula (I) may, depending on the nature of the substituents, be present as geometrical and/or as optically active isomers or corresponding isomer mixtures of varying composition. The invention relates to the pure isomers and to the isomer mixtures.

If appropriate, the compounds of the formula (I) may be present in various polymorphic forms or as mixtures of different polymorphic forms. The invention provides both the pure polymorphs and the polymorph mixtures, and both can be used according to the invention.

In the general formulae, alkyl denotes straight-chain or branched alkyl having preferably 1 to 6, in particular 1 to 4, carbon atoms. Examples which may be mentioned are methyl, ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,4-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl and 1-ethylbutyl.

Methyl, ethyl, n-propyl, isopropyl, n-butyl, isobutyl, sec-butyl and tert-butyl may be mentioned as being preferred.

Haloalkyl on its own or as a component of a radical in the general formulae comprises 1 to 4, in particular 1 to 3, carbon atoms having preferably 1 to 9, in particular 1 to 5, identical or different halogen atoms, preferably fluorine, chlorine or bromine, in particular fluorine or chlorine. Trifluoromethyl, trichloromethyl, chlorodifluoromethyl, dichlorofluoromethyl, chloromethyl, bromomethyl, 1-fluoroethyl, 2-fluoroethyl, 2,2-difluoroethyl, 2-chloro-2-fluoroethyl, 2,2,2-trifluoroethyl, 2,2,2-trichloroethyl, 2-chloro-2,2-difluoroethyl, pentafluoroethyl, 3-fluoropropyl, 2,2-difluoropropyl, 3,3,3-trifluoropropyl, 2,2,3,3,3-pentafluoropropyl and pentafluoro-tert-butyl may be mentioned by way of example and by way of preference.

2,2,2-trifluoroethyl, 2,2-difluoroethyl, 2-fluoroethyl and 3-fluoropropyl may be mentioned as being preferred.

If R¹ represents haloalkenyl this comprises 2 to 5, in particular 2 to 4, carbon atoms having preferably 1 to 4, in particular 1 to 3, identical or different halogen atoms, preferably fluorine, chlorine or bromine, in particular fluorine or chlorine. 2,2-difluoroethenyl, 3,3-difluoroprop-2-enyl, 3,3-dichloroprop-2-enyl, 4,4-difluorobut-3-enyl and 3,4,4-trifluorobut-3-enyl may be mentioned by way of example and by way of preference.

4,4-difluorobut-3-enyl and 3,4,4-trifluorobut-3-enyl may be mentioned by way of preference.

If R¹ represents halocycloalkyl, this comprises 3 to 5, in particular 3 to 4, carbon atoms having preferably 1 to 4, in particular 1 to 3, identical or different halogen atoms, preferably fluorine, chlorine or bromine, in particular fluorine or chlorine. 2-fluorocyclopropyl, 2,2-difluorocyclopropyl, 2-chlorocyclopropyl and 2,2-dichlorocyclopropyl may be mentioned by way of example.

2-fluorocyclopropyl may be mentioned as being preferred.

Alkylthio as component of a radical in the general formulae denotes straight-chain or branched alkylthio having preferably 1 to 6, in particular 1 to 4, carbon atoms. Methylthio, ethylthio, n-propylthio, isopropylthio, n-butylthio, isobutylthio, sec-butylthio and tert-butylthio may be mentioned by way of example.

Haloalkylthio as component of a radical in the general formulae denotes straight-chain or branched haloalkylthio having preferably 1 to 6, in particular 1 to 4, carbon atoms. Difluoromethylthio, trifluoromethylthio, trichloromethylthio, chlorodifluoromethylthio, 1-fluoroethylthio, 2-fluoroethylthio, 2,2-difluoromethylthio, 1,1,2,2-tetrafluoroethylthio, 2,2,2-trifluoroethylthio and 2-chloro-1,1,2-trifluoroethylthio may be mentioned by way of example.

Aryl is, for example, a mono-, di- or polycyclic aromatic radical, such as phenyl, naphthyl, tetra-hydronaphthyl, indanyl, fluoroenyl, and preferably phenyl or naphthyl, in particular phenyl.

Hetaryl represents, for example, pyridyl, pyrimidinyl, pyridazinyl, pyrazinyl, triazinyl, pyrazolyl, thiophenyl, oxazolyl, isoxazolyl, oxadiazolyl, thiadiazolyl, isothiazolyl, imidazolyl, pyrrolyl, furanyl, thiazolyl or triazolyl.

Heterocyclyl represents, for example, tetrahydrofuryl.

It is possible for two identical or different substituents to be present at the same atom.

The formula (I) provides a general definition of the compounds according to the invention.

Preferred substituents or ranges of the radicals listed in the formulae mentioned above and below are illustrated below.

A preferably represents tetrahydrofuryl or pyrid-3-yl which is optionally substituted in the 6-position by halogen, $C_1$-$C_4$-alkyl or $C_1$-$C_4$-halogenalkyl or represents pyrimidine-5-yl which is optionally substituted in the 2-position by halogen or $C_1$-$C_4$-alkyl or represents 1H-pyrazol-4-yl which is optionally substituted in the 1-position by $C_1$-$C_4$-alkyl and in the 3-position by halogen or represents 1H-pyrazol-5-yl which is optionally substituted in the 3-position by halogen or $C_1$-$C_4$-alkyl or represents isoxazol-5-yl which is optionally substituted in the 3-position by halogen or $C_1$-$C_4$-alkyl or represents 1,2,4-oxadiazol-5-yl which is optionally substituted in the 3-position by halogen or $C_1$-$C_4$-alkyl or represents 1-methyl-1,2,4-triazol-3-yl, 1,2,5-thiadiazol-3-yl or represents 1,3-thiazol-5-yl which is optionally substituted in the 2-position by halogen or $C_1$-$C_4$-alkyl.

A also preferably represents a radical

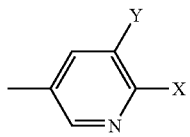

in which
X represents halogen, $C_1$-$C_4$-alkyl or $C_1$-$C_4$-halogenalkyl and
Y represents halogen, $C_1$-$C_4$-alkyl, $C_1$-$C_4$-halogenalkyl, $C_1$-$C_4$-halogenalkoxy, azido or cyano.

A also preferably represents a radical from the group consisting of 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-iodo-6-bromopyrid-3-yl, 5-fluoro-6-iodopyrid-3-yl, 5-chloro-6-iodopyrid-3-yl, 5-bromo-6-iodopyrid-3-yl, 5,6-diiodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl and 5-difluoromethyl-6-iodopyrid-3-yl.

A furthermore preferably represents a radical

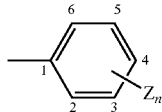

in which
n represents 2, 3 or 4 and
Z represents fluorine, chlorine or bromine.

$R^1$ preferably represents 2,2,2-trifluoroethyl or 2,2-difluoroethyl.

$R^2$ preferably represents in each case optionally fluorine-, chlorine- or bromine-substituted methyl, ethyl, n-propyl, isopropyl, n-butyl, isobutyl, sec-butyl, tert-butyl, cyclopropyl or cyclobutyl.

B preferably represents —$CR^3R^4$— or —$H_2C$—$CR^3R^4$—, in which
$R^3$ and $R^4$ independently of one another represent hydrogen, in each case optionally halogen- (especially fluorine-) substituted methyl, ethyl or $C_3$-$C_6$-cycloalkyl (especially cyclopropyl) or represent halogen, especially fluorine, or represent $C_1$-$C_4$-alkoxy-$C_1$-$C_4$-alkyl, especially methoxymethyl,
or
$R^3$ and $R^4$ together with the carbon atom to which they are attached form a 3- to 6-membered carbon ring.

If n represents 2, a first substituent Z is preferably located in the ortho position (2) and the second substituent Z is preferably located in the para position (4), or a first substituent Z is preferably located in the meta position (3) and the second substituent Z is preferably located in the para position (4) on the phenyl ring.

If n represents 3, a first substituent Z is preferably located in the ortho position (2) and the second substituent Z is preferably located in the para position (4) and the third substituent Z is preferably located in the meta position (3) on the phenyl ring.

The substituents Z can be identical or different.

A particularly preferably represents 6-chloropyrid-3-yl, 6-bromopyrid-3-yl, 6-methylpyrid-3-yl, 6-trifluoromethyl-pyrid-3-yl, 2-methylpyrimidin-5-yl, 2-chloropyrimid-5-yl, represents 1H-pyrazol-4-yl which is optionally substituted in the 1-position by methyl or ethyl and in the 3-position by chlorine, represents 1H-pyrazol-5-yl, 3-methylpyrazol-5-yl, 2-bromo-1,3-thiazol-5-yl, 2-chloro-1,3-thiazol-5-yl, represents isoxazol-5-yl which is optionally substituted in the 3-position by methyl, ethyl, chlorine or bromine, 3-methyl-1,2,4-oxadiazol-5-yl, 1-methyl-1,2,4-triazol-3-yl or 1,2,5-thiadiazol-3-yl.

A also particularly preferably represents 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl or 5-methyl-6-bromopyrid-3-yl.

A also particularly preferably represents a radical

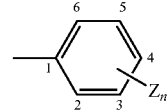

in which
n represents 2 or 3 and
Z represents fluorine or chlorine.

2,4-Dihalophenyl, in particular 2,4-dichlorphenyl, 2-fluoro-4-chlorophenyl, 2-chloro-4-fluorophenyl, 2,4-difluorophenyl; 3,4-dihalophenyl, in particular 3-fluoro-4-chlorophenyl, 3,4-dichlorophenyl, 3,4-difluorophenyl, 3-chloro-4-fluorophenyl; 3,4,6-trihalophenyl, in particular 4-chloro-3,6-difluorophenyl, 3,4-dichloro-6-fluorophenyl, 3,6-dichloro-4-fluorophenyl, 3-chloro-4,6-difluorophenyl, 4,6-dichloro-3-fluorophenyl, 3,4,6-trichlorophenyl, 3,4,6-trifluorophenyl, 6-chloro-3,4-difluorophenyl; 3,4,5-trihalophenyl, in particular 3,4,5-trichlorophenyl, 3,4-dichloro-5-fluorophenyl, 4-chloro-3,5-difluorophenyl, 3,4,5-trifluorophenyl, 3-chloro-4,5-difluorophenyl, 3,5-dichloro-4-fluorophenyl; 2,3,4-trihalophenyl, in particular 2,3,4-trichlorophenyl, 2-chloro-3,4-difluorophenyl, 2,4-dichloro-3-fluorophenyl, 2,3-dichloro-4-fluorophenyl, 2,3,4-trifluorophenyl, 3,4-dichloro-2-fluorophenyl, 4-chloro-2,3-difluorophenyl may be mentioned as particularly preferred radicals for A.

$R^1$ particularly preferably represents 2,2-difluoroethyl.

$R^2$ particularly preferably represents methyl or ethyl.

B particularly preferably represents a radical from the group consisting of (B-1) to (B-9)

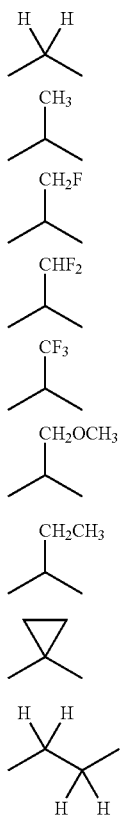

B-1
B-2
B-3
B-4
B-5
B-6
B-7
B-8
B-9

If n represents 2, a first substituent Z is particularly preferably located in the ortho position (2) and the second substituent Z is particularly preferably located in the para position (4) on the phenyl ring.

A very particularly preferably represents a radical from the group consisting of 6-chloropyrid-3-yl, 6-bromopyrid-3-yl, 2-methylpyrimidin-5-yl, 2-chloropyrimid-5-yl, 3-methylisoxazol-5-yl, 3-bromoisoxazol-5-yl, 5-fluoro-6-chloropyrid-3-yl, 5,6-dichloropyrid-3-yl, 5-fluoro-6-bromopyrid-3-yl, 2-chloro-1,3-thiazol-5-yl.

$R^1$ very particularly preferably represents 2,2-difluoroethyl.

$R^2$ very particularly preferably represents methyl.

B very particularly preferably represents methylene (—CH$_2$—).

In a special group of compounds of the formula (I), $R^2$ represents methyl, B represents methylene and A represents 2-chloropyrimidin-5-yl,

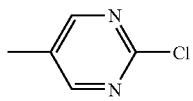

In a further special group of compounds of the formula (I), $R^2$ represents methyl, B represents methylene and A represents 5-fluoro-6-chloropyrid-3-yl,

In a further special group of compounds of the formula (I), $R^2$ represents methyl, B represents methylene and A represents 5,6-dichloropyrid-3-yl

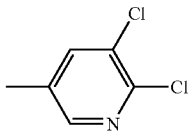

In a further special group of compounds of the formula (I), $R^2$ represents methyl, B represents methylene and A represents 5-bromo-6-chloropyrid-3-yl

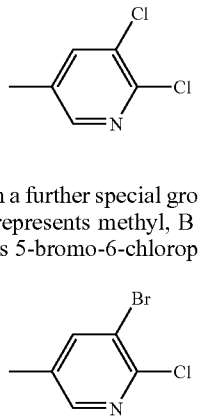

In a further special group of compounds of the formula (I), $R^2$ represents methyl, B represents methylene and A represents 5-methyl-6-chloropyrid-3-yl

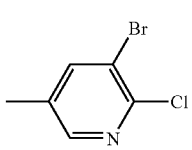

In a further special group of compounds of the formula (I), $R^2$ represents methyl, B represents methylene and A represents 5-fluoro-6-bromopyrid-3-yl

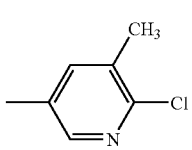

In a further special group of compounds of the formula (I), $R^2$ represents methyl, B represents methylene and A represents 5-chloro-6-bromopyrid-3-yl

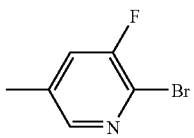

In a further special group of compounds of the formula (I), $R^2$ represents methyl, B represents methylene and A represents 5-chloro-6-iodopyrid-3-yl

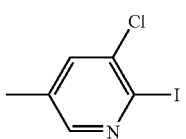

In a special group of compounds of the formula (I), $R^2$ represents methyl, B represents ethylene and A represents 2-chloropyrimidin-5-yl,

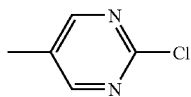

In a further special group of compounds of the formula (I), $R^2$ represents methyl, B represents ethylene and A represents 5-fluoro-6-chloropyrid-3-yl,

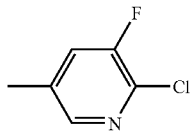

In a further special group of compounds of the formula (I), $R^2$ represents methyl, B represents methylene and A represents 5,6-dichloropyrid-3-yl

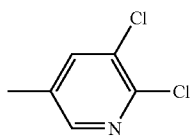

In a further special group of compounds of the formula (I), $R^2$ represents methyl, B represents methylene and A represents 5-bromo-6-chloropyrid-3-yl

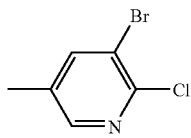

In a further special group of compounds of the formula (I), $R^2$ represents methyl, B represents methylene and A represents 5-methyl-6-chloropyrid-3-yl

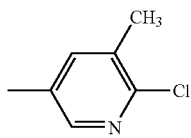

In a further special group of compounds of the formula (I), $R^2$ represents methyl, B represents methylene and A represents 5-fluoro-6-bromopyrid-3-yl

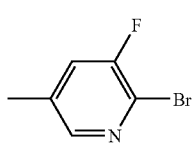

In a further special group of compounds of the formula (I), $R^2$ represents methyl, B represents methylene and A represents 5-chloro-6-bromopyrid-3-yl

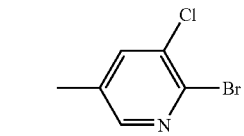

In a further special group of compounds of the formula (I), $R^2$ represents methyl, B represents methylene and A represents 5-chloro-6-iodopyrid-3-yl

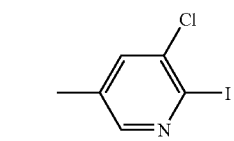

In a further special group of compounds of the formula (I), $R^2$ represents methyl, B represents methylene and A represents 2-chloropyrimidin-5-yl,

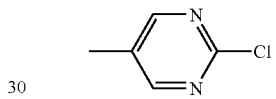

In a further special group of compounds of the formula (I), $R^2$ represents methyl, B represents methylene and A represents 5-fluoro-6-chloropyrid-3-yl,

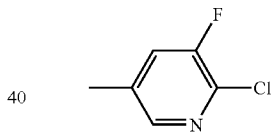

In a further special group of compounds of the formula (I), $R^2$ represents methyl, B represents methylene and A represents 5,6-dichloropyrid-3-yl,

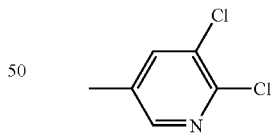

In a further special group of compounds of the formula (I), $R^2$ represents methyl, B represents methylene and A represents 5-bromo-6-chloropyrid-3-yl,

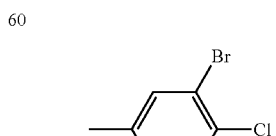

In a further special group of compounds of the formula (I), $R^2$ represents methyl, B represents methylene and A represents 5-methyl-6-chloropyrid-3-yl,

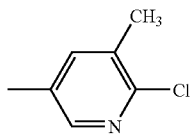

In a further special group of compounds of the formula (I), $R^2$ represents methyl, B represents methylene and A represents 5-fluoro-6-bromopyrid-3-yl,

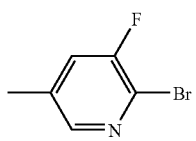

In a further special group of compounds of the formula (I), $R^2$ represents methyl, B represents methylene and A represents 5-chloro-6-bromopyrid-3-yl,

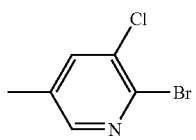

In a further special group of compounds of the formula (I), $R^2$ represents methyl, B represents methylene and A represents 5-chloro-6-iod-pyrid-3-yl

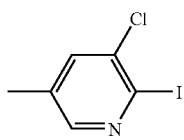

In a further special group of compounds of the formula (I), $R^1$ represents 2,2-difluoroethyl, $R^2$ represents methyl and B represents methylene.

In a further special group of compounds of the formula (I), $R^1$ represents 2,2,2-trifluoroethyl, $R^2$ represents methyl and B represents methylene.

In a further special group of compounds of the formula (I), $R^1$ represents 2-fluoroethyl, $R^2$ represents methyl and B represents methylene.

In a further special group of compounds of the formula (I), $R^1$ represents 3-fluoropropyl, $R^2$ represents methyl and B represents methylene.

In a further special group of compounds of the formula (I), $R^1$ represents 2,2-difluoroethyl, $R^2$ represents ethyl and B represents methylene.

In a further special group of compounds of the formula (I), $R^1$ represents 2,2,2-trifluoroethyl, $R^2$ represents ethyl and B represents methylene.

In a further special group of compounds of the formula (I), $R^1$ represents 2-fluoroethyl, $R^2$ represents ethyl and B represents methylene.

In a further special group of compounds of the formula (I), $R^1$ represents 3-fluoropropyl, $R^2$ represents ethyl and B represents methylene.

The general or preferred radical definitions or illustrations given above apply both to the end products and, correspondingly, to starting materials and intermediates. These radical definitions can also be combined with one another as desired, i.e. including combinations between the respective preferred ranges.

Preference according to the invention is given to compounds of the formula (I) which contain a combination of the meanings listed above as being preferred.

Particular preference according to the invention is given to compounds of the formula (I) which contain a combination of the meanings listed above as being particularly preferred.

Very particular preference according to the invention is given to compounds of the formula (I) which contain a combination of the meanings listed above as being very particularly preferred.

If, in the process 1 according to the invention for preparing the novel compounds of the general formula (I), in the first reaction step, the compound of the formula (II) used is, for example, methyl N-cyanoethanimide and the compound of the formula (III) used is, for example, 2,2-difluoroethaneamine, and the compound of the general formula (IV) formed in this manner, for example N'-cyano-N-(2,2-difluoroethyl)ethanimideamide, is reacted with a compound of the general formula (V), for example 6-chloro-3-chloromethylpyridine (CCMP), the preparation process 1 can be represented by reaction scheme I below:

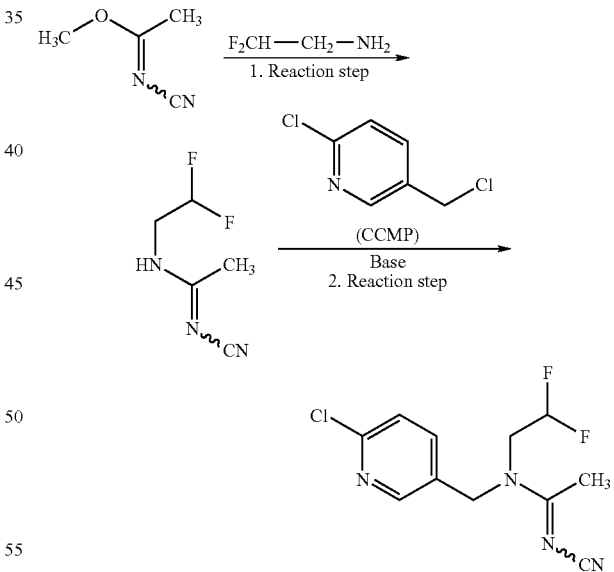

The formula (II) provides a general definition of the compounds required as starting materials for the first reaction step of the process 1 according to the invention.

In this formula (II), $R^2$ preferably represents those radicals which have already been mentioned in connection with the description of the compounds of the general formula (I) according to the invention as preferred substituents.

The compounds of the formula (II) are known (cf., for example, $R^2$=Me and Et, LG=OMe: B. Arnold, M. Regitz *Tetrahedron Lett.* (1980), 21, 909-912; A. A. Perez et al.

*Synthesis* (1983), 5, 402-404; R²=Me, LG=OEt: W. Lwowski, *Synthesis* 1971, 5, 263, DE 3 411 203 C1 (1985); R²=Et, LG=OEt: U.S. Pat. No. 4,734,413 A (1988); R²=n-Pr, LG=OMe: WO 93/00341 A1 (1993); R²=iso-Pr, LG=OMe: WO 19990617 (1999); R²=cyclo-Pr, LG=OMe: U.S. Pat. No. 4,670,559 (1988), or they can be prepared by known processes.

Orthoesters (cf. H. Schäfer, K. Gewald, *J. Prakt. Chem.* 1976, 318, 347-349) of the formula (VII), for example, can, as described in preparation process 3 below, be reacted according to methods known from the literature with cyanamide to give compounds of the formula (II) (LG=OR'; reaction scheme II; cf. also the preparation process 3 mentioned further below)

Scheme II

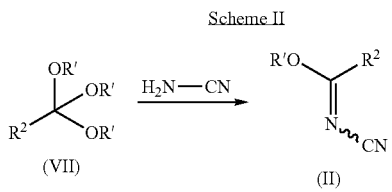

The formula (III) provides a general definition of the compounds further to be used as starting materials for carrying out the first reaction step of the process 1 according to the invention.

In the formula (III), $R^1$ is defined as already mentioned in connection with the description of the compounds of the formula (I) according to the invention.

The amino compounds of the formula (III) are commercially available, or they can be obtained in the manner known per se, for example according to the "Leuckart-Wallach reaction" (compounds of the general formula (III) in which $R^1$ represents alkyl, primary amines: cf., for example, Houbel-Weyl, Methoden der Organischen Chemie [Methods of Organic Chemistry], Vol. XI/1, 4 ed. 1957, G. Thieme Verlag, Stuttgart, p. 648; M. L. Moore in "The Leuckart Reaction" in: Organic Reactions, Vol. 5, 2 ed. 1952, New York, John Wiley & Sons, Inc. London). The 2,2-difluoroethylamine (cf. U.S. Pat. No. 4,030,994 (1977)) used in the first reaction step and the corresponding hydrochloride (A. Donetti et al., J. Med. Chem. 1989, 32, 957-961) are known.

The formula (V) provides a general definition of the compounds required as starting materials in the second reaction step of the process 1 according to the invention.

In this formula (V), A and B preferably represent those radicals which have already been mentioned in connection with the description of the compounds of the formula (I) according to the invention as preferred substituents.

E represents a suitable leaving group, as described further above.

General methods for preparing the starting materials (A-1) in which B represents a group —C($R^3R^4$)— and E denotes a suitable leaving group LG are shown in reaction scheme III.

Scheme III

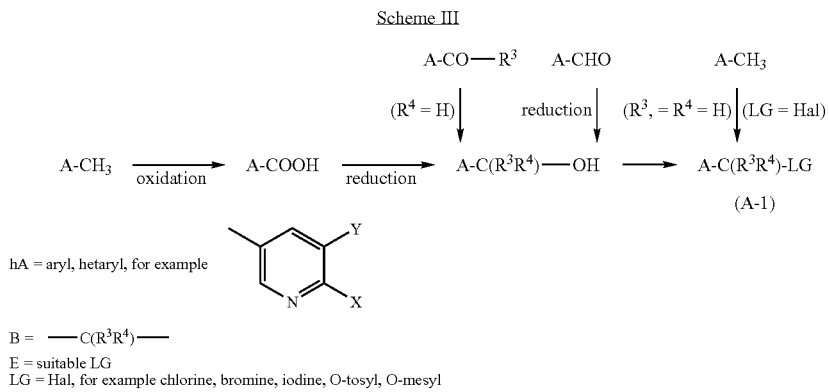

Some of the compounds (A-1, $R^3$, $R^4$=hydrogen) are known, or they can be obtained by known methods (for example 2-chloro-5-chloromethyl-1,3-thiazole: DE 3 631 538 (1988), EP 446 913 (1991), EP 780 384 (1997), EP 775 700 (1997), EP 794 180 (1997), WO 9 710 226 (1997); 6-chloro-3-chloromethylpyridine: DE 3 630 046 A1 (1988), EP 373 464 A2 (1990), EP 373 464 A2 (1990), EP 393 453 A2 (1990), EP 569 947 A1 (1993); 6-chloro-3-bromomethylpyridine: I. Cabanal-Duvillard et al., Heterocycl. Commun. 5, 257-262 (1999); 6-bromo-3-chloromethylpyridine, 6-bromo-3-hydroxymethylpyridine: U.S. Pat. No. 5,420,270 A (1995); 6-fluoro-3-chloromethylpyridine: J. A. Pesti et al., J. Org. Chem. 65, 7718-7722 (2000); 2-methyl-3-chloromethylpyridine: EP 302 389 A2 (1989); 2-trifluoromethyl-3-chloromethylpyridine: WO 2004082616 A2 (2004); 3-chloro-6-chloromethylpyridazine: EP 284 174 A1 (1988); 2-chloro-5-pyrazinylmethyl chloride: J. Heterocycl. Chem. 23, 149-151 (1986); 2-chloro-5-pyrazinylmethyl bromide: JP 05 239 034 A2 (1993).

Methyl-substituted aromatics or heterocycles of the formula $A-CH_3$ can be converted, for example, by oxidation into corresponding aromatic or heterocyclic carboxylic acids (A-COOH, for example 5-fluoro-6-bromonicotinic acid: F. L. Setliff, G. O. Rankin, J. Chem. Eng. Data (1972), 17, 515-516; 5-chloro-6-bromonicotinic acid and 5,6-dibromonicotinic acid: F. L. Setliff et al., J. Chem. Eng. Data (1981), 26, 332-333; 5-iodo-6-bromonicotinic acid: F. L. Setliff et al., J. Chem. Eng. Data (1978), 23, 96-97; 5-fluoro-6-iodonicotinic acid and 5-bromo-6-iodonicotinic acid: F. L. Setliff et al., J. Chem. Eng. Data (1973), 18, 449-450; 5-chloro-6-iodonicotinic acid: F. L. Setliff, J. E. Lane J. Chem. Eng. Data (1976), 21, 246-247 or carboxylic esters (for example methyl 5-methyl-6-fluoronicotinate: WO 9833772 A1, 1998; methyl 5-methyl-6-bromonicotinate: WO 9730032 A1, 1997). Also described in the prior art is the synthesis of formyl-substituted aromatics or heterocycles (A-CHO, for example 6-chloro-3-formyl-5-methylpyridine: DE 4429465 A1, 1996) from acyclic starting materials; this can be carried out, for example, by 1,3-dipolar cycloaddition (for example: 5-chloromethyl-3-bromoisoxazole: P. Pevarello, M. Varasi Synth. Commun. (1992), 22, 1939-1948).

The aromatic or heterocyclic carboxylic acids (A-COOH) or alkyl carbon compounds (A-CO—$R^3$; $R^3$=alkyl) can then be converted by methods known from the literature into the corresponding aromatic or heterocyclic hydroxyalkyl compounds (A-C($R^3R^4$)—OH; $R^3$=H, alkyl; $R^4$=H), which are then converted by methods known from the literature into activated aromatic or heterocyclic hydroxymethyl compounds (A-C($R^3R^4$)-LG, LG=O-tosyl, O-mesyl) or aromatic or heterocyclic halomethyl compounds (A-C($R^3R^4$)-LG, LG=Hal). The latter can also be obtained from corresponding methyl-substituted aromatics or heterocycles of the formula A-CH$_3$ using suitable halogenating agents known from the literature. An example of this approach which may be mentioned is the synthesis of the halomethyl-substituted heterocycles: 5-chloromethyl-2-methylpyrimidine (U. Eiermann et al., Chem. Ber. (1990), 123, 1885-9); 3-chloromethyl-5-bromo-6-chloropyridine, 3-bromo-5-iodo-6-chloropyridine (S. Kagabu et al., J. Pestic. Sci. (2005), 30, 409-413).

Starting materials (A-7) in which A represents a 5,6-disubstituted pyrid-3-yl radical can likewise be obtained by methods known from the literature. Suitable starting materials known from the literature are, for example, the 6-halo-substituted 5-nitro-β-picolines (A-2) which can be modified in accordance with known literature procedures, as shown in reaction scheme IV.

bromo-nicotinic acid: Setliff F. L., Rankin G. O. J. Chem. Engineering Data (1972), 17, 515-516; 5-bromo-6-fluoro-nicotinic acid, 5-bromo-6-chloro-nicotinic acid and 5-bromo-6-bromo-nicotinic acid: F. L. Setliff J. Chem. Engineering Data (1970), 15, 590-591; 5-chloro-6-bromo-nicotinic acid and 5-iodo-6-bromo-nicotinic acid: Setliff, F. L., Greene, J. S. J. Chem. Engineering Data (1978), 23, 96-97; also known as 5-chloro-6-trifluoromethyl-nicotinic acid: F. Cottet et al., Synthesis (2004), 10, 1619-1624), which can be converted in the presence of reducing agents into the corresponding hydroxymethylated pyridines (A-6) (for example 5-bromo-6-chloro-3-hydroxymethylpyridine: Kagabu, S. et al., J. Pestic. Sci. (2005), 30, 409-413).

Using 6-chloro-5-nitro-nicotinic acid (A-5, X=Cl, Y=NO$_2$; Boyer, J. H.; Schoen, W. J. Am. Chem. Soc. (1956), 78, 423-425) it is possible, by reduction, to form 6-chloro-3-hydroxymethyl-5-nitropyridine (A-6, X=Cl, Y=NO$_2$; Kagabu, S. et al., J. Med. Chem. (2000), 43, 5003-5009), which is subsequently reduced to 6-chloro-3-hydroxymethyl-5-aminopyridine (A-6, X=Cl, Y=NH$_2$; Kagabu, S. et al., J. Med. Chem. (2000), 43, 5003-5009) and, via diazotation and reaction with hydroxylamine, converted into 6-chloro-3-hydroxymethyl-5-azidopyridine (A-6, X=Cl, Y=N$_3$; Kagabu, S. et al., J. Med. Chem. (2000), 43, 5003-5009). Subsequent halogenation with thionyl chloride affords 6-chloro-3-chloromethyl-5-azidopyridine (A-7, X=Cl, Y=N$_3$, LG=Cl; Kagabu, S. et al., J. Med. Chem. (2000), 43, 5003-5009).

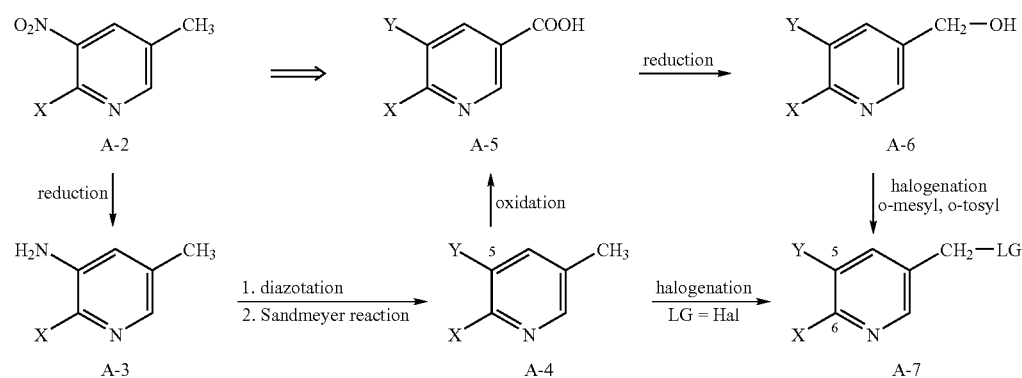

Scheme IV

X, Y = halogen, e.g. fluorine, chlorine, bromine, iodine
LG = halogen, O-mesyl, O-tosyl The reduction of the nitro group in 6-halo-substituted 5-nitro-β-picolines (A-2), for example, gives 6-halo-substituted 5-amino-β-picolines (A-3, for example 5-amino-6-chloro-β-picoline and 5-amino-6-bromo-β-picoline: Setliff, F. L. Org. Preparations and Preparations Int. (1971), 3, 217-222; Kagabu, S. et al. J. Pestic. Sci. (2005), 30, 409-413). Subsequent diazotation and Sandmeyer reaction (C. F. H. Allen, J. R. Thirtle, Org. Synth., Coll. Vol. III, 1955, p. 136) allows halogen substitutes to be introduced in the 5-position (A4, for example 5-fluoro-6-chloro-β-picoline and 5-fluoro-6-bromo-β-picoline: Setliff, F. L. Org. Preparations and Preparations Int. (1971), 3, 217-222; 5-iodo-6-chloro-β-picoline: Kagabu, S. et al. J. Pestic. Sci. (2005), 30, 409-413; 5,6-dichloropicoline: Setliff, F. L.; Lane, J. E. J. Chem. Engineering Data (1976), 21, 246-247). Oxidation of the methyl group in the 5,6-disubstituted β-picolines (A-4) then affords the corresponding 5,6-disubstituted nicotinic acids (A-5, for example 5-fluoro-6-chloro-nicotinic acid and 5-fluoro-6-

Alternatively, halogenation of the methyl group in the 3-position of (A-4) yields the compounds (A-7) in which LG represents halogen (for example: 3-bromomethyl-6-chloro-5-fluoropyridine, 3-bromomethyl-6-chloro-5-iodopyridine: Kagabu, S. et al. J. Pestic. Sci. (2005), 30, 409-413). If 6-halo-substituted 5-nitro-β-picolines (A-4; Y=NO$_2$) are used, the methyl group in the 3-position may be halogenated first (for example 3-bromomethyl-6-chloro-5-nitropyridine: Kagabu, S. et al., J. Pestic. Sci. (2005), 30, 409-413). If appropriate, the nitro group may also be reduced at a later point in the reaction sequence.

Likewise known from the literature is the introduction of substituents in the 5-position (for example Y=N$_3$) of compounds (A-7) in which LG represents n-morpholino. This radical can then be replaced in a very simple manner by halogen (LG=Hal) (cf. S. Kagabu et al., J. Med. Chem. 2000, 43, 5003-5009; reaction conditions: ethyl chloroformate, tetrahydrofuran, 60° C.).

In general, it is possible to replace halogen atoms in the vicinity of the pyridine nitrogen by other halogen atoms or halogenated groups, for example trifluoromethyl (transhalogenation, for example: chlorine for bromine or iodine; bromine for iodine or fluorine; iodine for fluorine or trifluoromethyl). Accordingly, a further alternative synthesis route comprises replacing the halogen atom (for example X=Cl) in the 6-position of the pyrid-5-yl radical (for example in A-5 where X, Y=Cl; 5,6-dichloronicotinic acid: Setliff, F. L.; Lane, J. E. J. Chem. Engineering Data (1976), 21, 246-247) by another halogen atom, for example iodine or fluorine (for example: A-5 where X=I; 5-bromo-6-iodonicotinic acid, and A-5 where X=F; 5-bromo-6-fluoronicotinic acid: Setliff, F. L.; Price, D. W. J. Chem. Engineering Data (1973), 18, 449-450). However, this transhalogenation may, if appropriate, be carried out later with suitable compounds of the formula (I).

In general, it is advantageous to carry out the preparation process 1 according to the invention in the presence of diluents, if appropriate, and in the presence of basic reaction auxiliaries, if appropriate.

Diluents are advantageously employed in an amount such that the reaction mixture remains readily stirrable during the entire process. Suitable diluents for carrying out the process 1 according to the invention are all inert organic solvents.

Examples which may be mentioned are: halogenated hydrocarbons, in particular chlorinated hydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols, such as methanol, ethanol, isopropanol, butanol; ethers, such as ethyl propyl ether, methyl tert-butyl ether, n-butyl ether, anisol, phenetol, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide; amines, such as trimethylamine, triethylamine, tripropylamine, tributylamine, N-methylmorpholine, pyridine and tetramethylenediamine; nitrated hydrocarbons, such as nitromethane, nitroethane, nitropropane, nitrobenzene, chloronitrobenzene, o-nitrotoluene; nitriles, such as acetonitrile, propionitrile, butyronitrile, isobutyronitrile, benzonitrile, m-chlorobenzonitrile, and also compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones, such as dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone; aliphatic, cycloaliphatic or aromatic hydrocarbons, such as pentane, hexane, heptane, octane, nonane and industrial hydrocarbons; for example white spirits comprising components having boiling points in the range of, for example, from 40° C. to 250° C., cymol, benzene fractions within a boiling point interval of from 70° C. to 190° C., cyclohexane, methylcyclohexane, petroleum ether, ligroin, octane, benzene, toluene, chlorobenzene, bromobenzene, nitrobenzene, xylene; esters, such as methyl acetate, ethyl acetate, butyl acetate, isobutyl acetate, and also dimethyl carbonate, dibutyl carbonate, ethylene carbonate; amides, such as hexamethylenephosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazo-linedione, N-formylpiperidine, N,N'-1,4-diformylpiperazine; ketones, such as acetone, acetophenone, methyl ethyl ketone, methyl butyl ketone.

It is, of course, also possible to use mixtures of the solvents and diluents mentioned for the process according to the invention.

However, preferred diluents for carrying out the first reaction step of the preparation process 1 according to the invention are alcohols, such as methanol, ethanol, isopropanol or butanol.

Preferred diluents for carrying out the second reaction step of the preparation process 1 according to the invention are nitriles, such as acetonitrile, propionitrile, butyronitrile, isobutyronitrile, benzonitrile or m-chlorobenzonitrile, in particular acetonitrile.

Suitable for use as basic reaction auxiliaries for carrying out the second reaction step of the preparation process 1 according to the invention are all suitable acid binders, such as amines, in particular tertiary amines, and also alkali metal and alkaline earth metal compounds.

Examples of these which may be mentioned are the hydroxides, hydrides, oxides, bicarbonates and carbonates of lithium, sodium, potassium, cesium, magnesium, calcium and barium, furthermore, further basic compounds, such as amidine bases or guanidine bases, such as 7-methyl-1,5,7-triaza-bicyclo[4.4.0]dec-5-ene (MTBD), diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, penta-methylpiperidine, tertiary amines, such as triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazol, N-methylpyrazole, N-methylmorpholine, N-methylhexamethylenediamine, pyridine, 4-pyrrolidinopyridine, 4-dimethylaminopyridine, quinoline, α-picoline, β-picoline, isoquinoline, pyrimidine, acridine, N,N,N',N'-tetramethylenediamine, N,N',N'-tetramethylenediamine, quinoxaline, N-propyldiisopropylamine, N-ethyldiisopropylamine, N,N'-dimethylcyclohexylamine, 2,6-lutidine, 2,4-lutidine or triethyldiamine.

Preference is given to using salts of cesium, for example cesium carbonate or cesium iodide.

The reaction of the compounds of the formula (II) according to the first reaction step of the preparation process 1 is carried out by reacting the compounds of the formula (II) in the presence of compounds of the formula (III) and one of the stated diluents.

The reaction time is from 5 minutes to 48 hours. The reaction is carried out at temperatures between −100° C. and +200° C., preferably between −50° C. and 150° C., particularly preferably at room temperature.

In principle, the reaction can be carried out under atmospheric pressure. Preferably, the reaction is carried out under atmospheric pressure or under pressures of up to 15 bar and, if appropriate, under an atmosphere of protective gas (nitrogen, helium or argon).

For carrying out the first reaction step of the preparation process 1 according to the invention, in general from 0.5 to 4.0 mol, preferably from 0.7 to 3.0 mol, particularly preferably from 1.0 to 2.0 mol, of the compounds of the formula (III) are employed per mole of the compound of the general formula (II).

After the reaction has ended, the entire reaction mixture is concentrated. The products obtained after work-up can be purified in a customary manner by recrystallization, distillation under reduced pressure or column chromatography (cf. also the Preparation Examples).

The reaction of compounds of the formula (IV) according to the second reaction step of the preparation process 1 is carried out by reacting the compounds of the general formula (IV) in the presence of compounds of the formula (V) in one of the stated diluents and in the presence of a basic reaction auxiliary.

The reaction time is from 5 minutes to 48 hours. The reaction is carried out at temperatures between −100° C. and +200° C., preferably between −50° C. and 150° C., particularly preferably at the reflux temperature of the solvent indicated further above.

In principle, the reaction can be carried out under atmospheric pressure. Preferably, the reaction is carried out under atmospheric pressure or under pressures of up to 15 bar and, if appropriate, under an atmosphere of protective gas (nitrogen, helium or argon).

For carrying out the second reaction step of the preparation process 1 according to the invention, in general from 0.5 to 4.0 mol, preferably from 0.7 to 3.0 mol, particularly preferably from 1.0 to 2.0 mol, of the compounds of the formula (V) are employed per mole of the compound of the general formula (IV).

After the reaction has ended, the entire reaction mixture is concentrated. The products obtained after work-up can be purified in a customary manner by recrystallization, distillation under reduced pressure or column chromatography (cf. also the Preparation Examples).

If, in the preparation process 2 according to the invention for preparing novel compounds of the formula (I), as compound of the formula (II), for example, methyl N-cyanoethanimide, is reacted with the compound of the formula (VI), for example with N-[(6-chloro-5-fluoropyridin-3-yl)methyl]-2,2-difluoroethylamine, the preparation process 2 can be represented by reaction scheme V:

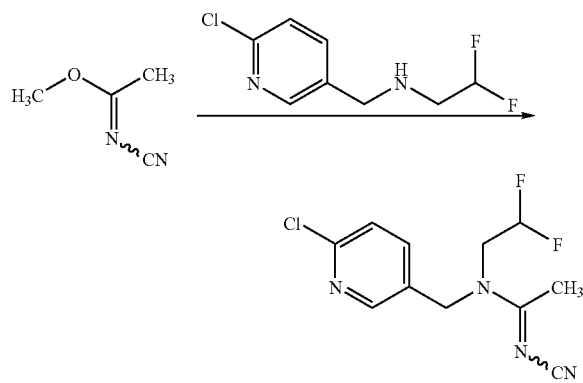

The formula (II) provides a general definition of the compounds required as starting materials for the process 2 according to the invention.

In this formula (II), $R^2$ preferably represents those radicals which have already been mentioned in connection with the description of the compounds of the general formula (I) according to the invention a preferred substituents.

The compounds of the formula (II) can be obtained by preparation process 1, described further above, from orthoester and cyanamide (cf. Scheme II).

The formula (VI) provides a general definition of the compounds further to be used as starting materials for carrying out the process 2 according to the invention.

In formula (VI), A, B and $R^1$ have the meaning already mentioned for substituents in connection with the description of the compounds of the general formula (I) according to the invention.

For preparing the starting materials (A-8) in which B represents $C(R^3R^4)$, it is advantageous to react, for example, compounds of the formula (A-1) which A has the meaning mentioned further above and LG represents a suitable leaving group (for example chlorine, bromine, iodine, o-tosyl, o-mesyl) with compounds of the general formula (A-9) in which R' represents halogen-containing alkyl, if appropriate in the presence of diluents and if appropriate in the presence of the basic reaction auxiliaries mentioned in preparation process 1 (cf. reaction scheme VI).

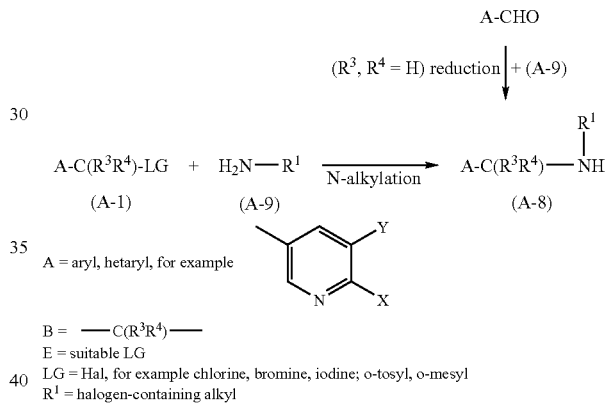

A = aryl, hetaryl, for example

B = —C($R^3R^4$)—
E = suitable LG
LG = Hal, for example chlorine, bromine, iodine; o-tosyl, o-mesyl
$R^1$ = halogen-containing alkyl Alternatively and in certain cases, however, it is also possible to prepare starting materials (A-8) in which $R^3$ and $R^4$ represents hydrogen from the corresponding aldehydes (A-CHO) and the compounds (A-9) by reductive amination (cf. Houben-Weyl, Methoden der Organischen Chemie, Vol. XI/1, page 602, G. Thieme Verlag, Stuttgart, Germany).

In general, it is advantageous to carry out the preparation process 2 according to the invention in the presence of one of the diluents mentioned further above, if appropriate.

The reaction of compounds of the formula (II) according to preparation process 2 is carried out by reacting these compounds with compounds of the formula (VI).

The reaction time is from 5 minutes to 48 hours. The reaction is carried out at temperatures between −100° C. and +200° C., preferably between −50° C. and 150° C.

In principle, the reaction can be carried out under atmospheric pressure. Preferably, the reaction is carried out under atmospheric pressure or under pressures of up to 15 bar and, if appropriate, under an atmosphere of protective gas (nitrogen, helium or argon).

For carrying out the preparation process 2 according to the invention, in general from 0.5 to 4.0 mol, preferably from 0.7 to 3.0 mol, particularly preferably from 1.0 to 2.0 mol, of the compounds of the formula (VII) are employed per mole of the compound of the general formula (II).

After the reaction has ended, the entire reaction mixture is concentrated. The products obtained after work-up can be purified in a customary manner by recrystallization, distillation under reduced pressure or column chromatography (cf. also the Preparation Examples).

If, in the preparation process 3 according to the invention for preparing the novel compounds of the formula (I), in the first reaction step, the compound of the formula (VII) employed is, for example, methyl orthoacetate in the presence of cyanamide, and the compounds of the formula (II) formed in situ, for example methyl N-cyanoethanimidate, are reacted in a second step with compounds of the formula (VIII), for example with 3-aminomethyl-6-chloropyridine, to give compounds of the formula (IX), for example N'-cyano-N-[6-chloropyrid-3-ylmethyl]ethanimidamide, and the latter is, in the third reaction step, N-alkylated in the presence of compounds of the formula (X), for example with 2,2-difluoroethyl bromide, preparation process 3 may be represented by reaction scheme VII:

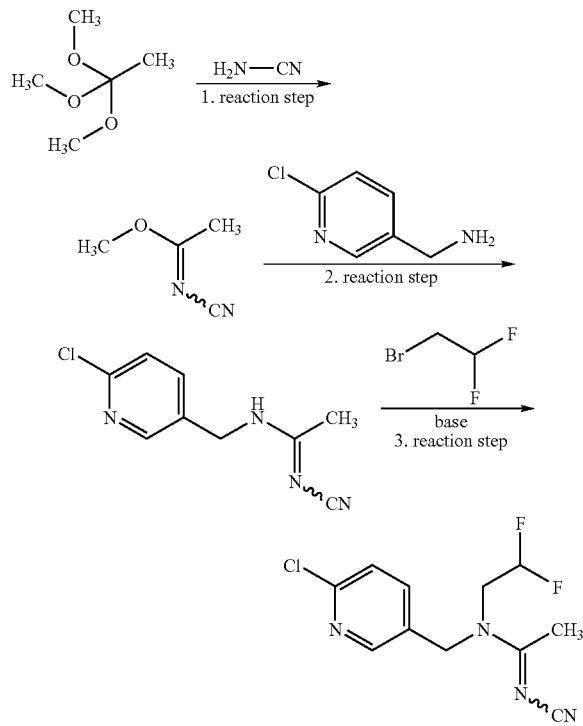

The formula (VII) provides a general definition of the compounds required as starting materials for process 3 according to the invention.

In this formula (VII), $R^2$ preferably represents those radicals which have already been mentioned in connection with the description of the compounds of the general formula (I) according to the invention as preferred substituents. In this formula (VII), R' preferably represents $C_1$-$C_4$-alkyl, in particular methyl or ethyl.

The compounds of the formula (VII) and cyanamide are known compounds (cf. also H. Schäfer, K. Gewald, *J. Prakt. Chem.* 1976, 318, 347-349).

The formula (VIII) provides a general definition of the compounds further to be used as starting materials for carrying out the first reaction step in process 3 according to the invention.

In formula (VIII), A and B have the meaning already mentioned for substituents in connection with the description of the compounds of the general formula (I) according to the invention.

The first two reaction steps of the preparation process 3 according to the invention can be carried out analogously to H. Schäfer, K. Gewald, *J. Prakt. Chem.* 1976, 318, 347-349 (Synthesis of arylaminoethylenecyanamides) and to working example 1 in WO 03/095418 A1 (N'-cyano-N-aryl-ethyl)propanimidamide). Preferred is a one pot process which, if appropriate, can be carried out in the absence of a diluent (depending on the orthoester in question).

The reaction of compounds of the formula (II) in accordance with the first two reaction steps of preparation process 3 is carried out by reacting the compounds of the formula (VI) in the presence of cyanamide and of compounds of the formula (VIII).

The reaction time is from 5 minutes to 48 hours. The reaction is carried out at temperatures between −100° C. and +200° C., preferably between −50° C. and 150° C., particularly preferably at the boiling point of the orthoester in question.

In principle, the reaction can be carried out under atmospheric pressure. Preferably, the reaction is carried out under atmospheric pressure or under pressures of up to 15 bar and, if appropriate, under an atmosphere of protective gas (nitrogen, helium or argon).

For carrying out the preparation process 3 according to the invention, in general from 0.5 to 4.0 mol, preferably from 0.7 to 3.0 mol, particularly preferably from 1.0 to 2.0 mol, of cyanamide and of the compounds of the formula (VIII) are employed per mole of the compound of the general formula (II).

After the reaction has ended, the entire reaction mixture is concentrated. The compounds of the formula (IX) obtained after work-up can be purified in a customary manner by recrystallization, distillation under reduced pressure or column chromatography (cf. also the Preparation Examples).

The formula (X) provides a general definition of the compounds furthermore to be used as starting materials for carrying out the third reaction step in the process 3 according to the invention.

In the formula (X), $R^1$ has the meaning already mentioned in connection with the description of the compounds of the general formula (I) according to the invention.

E represents a suitable leaving group, as described further above.

Some of the compounds of the formula (X) can be obtained commercially or by methods known from the literature (cf. compounds of the formula (X) in which E represents halogen, such as chlorine, bromine and iodine: Houben-Weyl, Methoden der Organischen Chemie, Volume V/3, p. 503 and Volume V/4 p. 13, 517, G. Thieme Verlag, Stuttgart, Germany; $E^1$ represents mesylate: Crossland, R. K., Servis, K. L. *J. Org. Chem.* (1970), 35, 3195; E represents tosylate: Roos, A. T. et al., *Org. Synth.*, Coll. Vol. I, (1941), 145; Marvel, C. S., Sekera, V. C. *Org. Synth.*, Coll. Vol. III, (1955), 366. The halogenated alkanes used are known, for example, from the literature (cf. $R^1$=$CH_2CHF_2$, E=Br, 2,2-difluoroethyl bromide: EP 420815; $R^1$=$CH_2CHF_2$, E=I, 2,2-difluoroethyliodide: A. Kamal et al., *Tetrahedron Lett.* (2002), 43, 7353-7355; $R^1$=$CH_2CHF_2$, E=$OSO_2Me$, 2,2-difluoroethyl methanesulphonate: DE 4315371, WO 2002044145).

In general, it is advantageous to carry out the third reaction step of the preparation process 3 according to the invention in the presence of diluents and in the presence of basic reaction auxiliaries.

Preferred diluents for carrying out the third reaction step of the preparation process 3 according to the invention are amides, such as hexamethylenephosphoric triamide, formamide, N-methyl-formamide, N,N-dimethylformamide, N,N-dipropylformamide, N,N-dibutylformamide, N-methylpyrrolidine, N-methylcaprolactam, in particular N,N-dimethylformamide.

Preferred for use as basic reaction auxiliaries for carrying out the third reaction step of the preparation process 3 according to the invention are hydrides or carbonates of alkali metals, for example of lithium, sodium, potassium or cesium.

For carrying out the third reaction step of preparation process 3 according to the invention, in general from 0.5 to 4.0 mol, preferably from 0.7 to 3.0 mol, particularly preferably from 1.0 to 2.0 mol, of compounds of the formula (X) are employed per mole of the compound of the formula (IX).

The reaction time for the third reaction step is from 5 minutes to 48 hours. The reaction is carried out at temperatures between −10° C. and +200° C., preferably between +10° C. and 180° C., particularly preferably between 20° C. and 140° C. In principle, the reaction can be carried out under atmospheric pressure. Preferably, the reaction is carried out under atmospheric pressure or under pressures of up to 15 bar and, if appropriate, under an atmosphere of protective gas.

For carrying out the first reaction step of preparation process 3 according to the invention, in general from 0.5 to 4.0 mol, preferably from 0.7 to 3.0 mol, particularly preferably from 1.0 to 2.0 mol, of compounds of the formula (VIII) are employed per mole of the compound of the formula (II).

After the reaction has ended, the entire reaction mixture is concentrated. The products obtained after work-up can be purified in a customary manner by recrystallization, distillation under reduced pressure or column chromatography (cf. also the Preparation Examples).

In addition to what is stated above with respect to the preparation processes, reference is made to the preparation examples.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and mollusks, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Stemechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Dermaptera, for example, *Forficula auricularia.*

From the order of the Diplopoda, for example, *Blaniulus guttulatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuellebomi, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control Protozoa, such as Eimeria.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Dicono-* coris hewetti, Dysdercus spp., Euschistus spp., Eurygaster spp., Heliopeltis spp., Horcias nobilellus, Leptocorisa spp., Leptoglossus phyllopus, Lygus spp., Macropes excavatus, Miridae, Nezara spp., Oebalus spp., Pentomidae, Piesma quadrata, Piezodorus spp., Psallus seriatus, Pseudacysta persea, Rhodnius spp., Sahlbergella singularis, Scotinophora spp., Stephanitis nashi, Tibraca spp., Triatoma spp.

From the order of the Homoptera, for example, Acyrthosipon spp., Aeneolamia spp., Agonoscena spp., Aleurodes spp., Aleurolobus barodensis, Aleurothrixus spp., Amrasca spp., Anuraphis cardui, Aonidiella spp., Aphanostigma piri, Aphis spp., Arboridia apicalis, Aspidiella spp., Aspidiotus spp., Atanus spp., Aulacorthum solani, Bemisia spp., Brachycaudus helichrysii, Brachycolus spp., Brevicoryne brassicae, Calligypona marginata, Cameocephala fulgida, Ceratovacuna lanigera, Cercopidae, Ceroplastes spp., Chaetosiphon fragaefolii, Chionaspis tegalensis, Chlorita onukii, Chromaphis juglandicola, Chrysomphalus ficus, Cicadulina mbila, Coccomytilus halli, Coccus spp., Cryptomyzus ribis, Dalbulus spp., Dialeurodes spp., Diaphorina spp., Diaspis spp., Doralis spp., Drosicha spp., Dysaphis spp., Dysmicoccus spp., Empoasca spp., Eriosoma spp., Erythroneura spp., Euscelis bilobatus, Geococcus coffeae, Homalodisca coagulata, Hyalopterus arundinis, Icerya spp., Idiocerus spp., Idioscopus spp., Laodelphax striatellus, Lecanium spp., Lepidosaphes spp., Lipaphis erysimi, Macrosiphum spp., Mahanarva fimbriolata, Melanaphis sacchari, Metcalfiella spp., Metopolophium dirhodum, Monellia costalis, Monelliopsis pecanis, Myzus spp., Nasonovia ribisnigri, Nephotettix spp., Nilaparvata lugens, Oncometopia spp., Orthezia praelonga, Parabemisia myricae, Paratrioza spp., Parlatoria spp., Pemphigus spp., Peregrinus maidis, Phenacoccus spp., Phloeomyzus passerinii, Phorodon humuli, Phylloxera spp., Pinnaspis aspidistrae, Planococcus spp., Protopulvinaria pyriformis, Pseudaulacaspis pentagona, Pseudococcus spp., Psylla spp., Pteromalus spp., Pyrilla spp., Quadraspidiotus spp., Quesada gigas, Rastrococcus spp., Rhopalosiphum spp., Saissetia spp., Scaphoides titanus, Schizaphis graminum, Selenaspidus articulatus, Sogata spp., Sogatella furcifera, Sogatodes spp., Stictocephala festina, Tenalaphara malayensis, Tinocallis caryaefoliae, Tomaspis spp., Toxoptera spp., Trialeurodes vaporariorum, Trioza spp., Typhlocyba spp., Unaspis spp., Viteus vitifolii.

From the order of the Hymenoptera, for example, Diprion spp., Hoplocampa spp., Lasius spp., Monomorium pharaonis, Vespa spp.

From the order of the Isopoda, for example, Armadillidium vulgare, Oniscus asellus, Porcellio scaber.

From the order of the Isoptera, for example, Reticulitermes spp., Odontotermes spp.

From the order of the Lepidoptera, for example, Acronicta major, Aedia leucomelas, Agrotis spp., Alabama argillacea, Anticarsia spp., Barathra brassicae, Bucculatrix thurberiella, Bupalus piniarius, Cacoecia podana, Capua reticulana, Carpocapsa pomonella, Chematobia brumata, Chilo spp., Choristoneura fumiferana, Clysia ambiguella, Cnaphalocerus spp., Earias insulana, Ephestia kuehniella, Euproctis chrysorrhoea, Euxoa spp., Feltia spp., Galleria mellonella, Helicoverpa spp., Heliothis spp., Hofmannophila pseudospretella, Homona magnanima, Hyponomeuta padella, Laphygma spp., Lithocolletis blancardella, Lithophane antennata, Loxagrotis albicosta, Lymantria spp., Malacosoma neustria, Mamestra brassicae, Mocis repanda, Mythimna separata, Oria spp., Oulema oryzae, Panolis flammea, Pectinophora gossypiella, Phyllocnistis citrella, Pieris spp., Plutella xylostella, Prodenia spp., Pseudaletia spp., Pseudoplusia includens, Pyrausta nubilalis, Spodoptera spp., Thermesia gemmatalis, Tinea pellionella, Tineola bisselliella, Tortrix viridana, Trichoplusia spp.

From the order of the Orthoptera, for example, Acheta domesticus, Blatta orientalis, Blattella germanica, Gryllotalpa spp., Leucophaea maderae, Locusta spp., Melanoplus spp., Periplaneta americana, Schistocerca gregaria.

From the order of the Siphonaptera, for example, Ceratophyllus spp., Xenopsylla cheopis.

From the order of the Symphyla, for example, Scutigerella immaculata.

From the order of the Thysanoptera, for example, Baliothrips biformis, Enneothrips flavens, Frankliniella spp., Heliothrips spp., Hercinothrips femoralis, Kakothrips spp., Rhipiphorothrips cruentatus, Scirtothrips spp., Taeniothrips cardamoni, Thrips spp.

From the order of the Thysanura, for example, Lepisma saccharina.

The phytoparasitic nematodes include, for example, Anguina spp., Aphelenchoides spp., Belonoaimus spp., Bursaphelenchus spp., Ditylenchus dipsaci, Globodera spp., Heliocotylenchus spp., Heterodera spp., Longidorus spp., Meloidogyne spp., Pratylenchus spp., Radopholus similis, Rotylenchus spp., Trichodorus spp., Tylenchorhynchus spp., Tylenchulus spp., Tylenchulus semipenetrans, Xiphinema spp.

The compounds of the formula (I) according to the invention have in particular excellent activity against . . . .

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or —POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or lattices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

Particularly favourable mixing components are, for example, the following:

Fungicides:
Inhibitors of Nucleic Acid Synthesis
    benalaxyl, benalaxyl-M, bupirimate, chiralaxyl, clozylacon, dimethirimol, ethirimol, furalaxyl, hymexazol, mefenoxam, metalaxyl, metalaxyl-M, ofurace, oxadixyl, oxolinic acid Inhibitors of Mitosis and Cell Division
    benomyl, carbendazim, diethofencarb, ethaboxam, fuberidazole, pencycuron, thiabendazole, thiophanate-methyl, zoxamide Inhibitors of Respiratory Chain Complex I
    diflumetorim Inhibitors of Respiratory Chain Complex II
    boscalid, carboxin, fenfuram, flutolanil, furametpyr, furmecyclox, mepronil, oxycarboxin, penthiopyrad, thifluzamide Inhibitors of Respiratory Chain Complex III
    azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin Decouplers
    dinocap, fluazinam Inhibitors of ATP Production
    fentin acetate, fentin chloride, fentin hydroxide, silthiofam Inhibitors of Amino Acid Biosynthesis and Protein Biosynthesis
    andoprim, blasticidin-S, cyprodinil, kasugamycin, kasugamycin hydrochloride hydrate, mepanipyrim, pyrimethanil Inhibitors of Signal Transduction
    fenpiclonil, fludioxonil, quinoxyfen Inhibitors of Lipid and Membrane Synthesis
    chlozolinate, iprodione, procymidone, vinclozolin
    ampropylfos, potassium-ampropylfos, edifenphos, etridiazole, iprobenfos (IBP), isoprothiolane, pyrazophos
    tolclofos-methyl, biphenyl
    iodocarb, propamocarb, propamocarb hydrochloride, propamocarb-fosetylate Inhibitors of Ergosterol Biosynthesis
    fenhexamid,
    azaconazole, bitertanol, bromuconazole, cyproconazole, diclobutrazole, difenoconazole, diniconazole, diniconazole-M, epoxiconazole, etaconazole, fenarimol, fenbuconazole, fluquinconazole, flurprimidole, flusilazole, flutriafol, furconazole, furconazole-cis, hexaconazole, imazalil, imazalil sulphate, imibenconazole, ipconazole, metconazole, myclobutanil, nuarimol, oxpoconazole, paclobutrazole, penconazole, pefurazoate, prochloraz, propiconazole, prothioconazole, pyrifenox, simeconazole, tebuconazole, tetraconazole, triadimefon, triadimenol, triflumizole, triforine, triticonazole, uniconazole, voriconazole, viniconazole,
    aldimorph, dodemorph, dodemorph acetate, fenpropidin, fenpropimorph, spiroxamine, tridemorph,
    naftifine, pyributicarb, terbinafine Inhibitors of Cell Wall Synthesis
　　benthiavalicarb, bialaphos, dimethomorph, flumorph, iprovalicarb, mandipropamid, polyoxins, polyoxorim, validamycin A
Inhibitors of Melanin Biosynthesis
　　capropamid, diclocymet, fenoxanil, phthalid, pyroquilon, tricyclazole
Resistance Inductors
　　acibenzolar-S-methyl, probenazole, tiadinil
Multisite
　　captafol, captan, chlorothalonil, copper salts such as: copper hydroxide, copper naphthenate, copper oxychloride, copper sulphate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram
Further Fungicides
　　amibromdol, benthiazole, bethoxazin, capsimycin, carvone, quinomethionate, chloropicrin, cufraneb, cyflufenamid, cymoxanil, dazomet, debacarb, diclomezine, dichlorophen, dicloran, difenzoquat, difenzoquat metilsulphate, diphenylamine, ferimzone, flumetover, flusulphamide, fluopicolide, fluoroimide, fosetyl-aluminium, fosetyl-calcium, fosetyl-sodium, hexachlorobenzene, 8-hydroxyquinoline sulphate, irumamycin, methasulphocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyribencarb, pyrrolnitrin, quintozene, tecloftalam, tecnazene, triazoxide, trichlamide, valiphenal, zarilamid,
2-(2-{[6-(3-chloro-2-methylphenoxy)-5-fluoropyrimidin-4-yl]oxy}phenyl)-2-(methoxyimino)-N-methylacetamide,
2-[[[[1-[3-(1-fluoro-2-phenylethyl)oxy]phenyl]ethylidene]amino]oxy]methyl]-alpha-(methoxyimino)-N-methyl-alpha-benzacetamide,
cis-1-(4-chlorophenyl)-2-(1H-1,2,4-triazol-1-yl)cycloheptanol,
1-[(4-methoxyphenoxy)methyl]-2,2-dimethylpropyl-1H-imidazole-1-carboxylic acid,
2,3,5,6-tetrachloro-4-(methylsulphonyl)pyridine,
2-butoxy-6-iodo-3-propylbenzopyranon-4-one,
2-chloro-N-(2,3-dihydro-1,1,3-trimethyl-1H-inden-4-yl)-3-pyridinecarboxamide,
3,4,5-trichloro-2,6-pyridinedicarbonitrile,
3,4-dichloro-N-(2-cyanophenyl)isothiazole-5-carboxamide (isotianil)
3-[5-(4-chlorophenyl)-2,3-dimethylisoxazolidin-3-yl]pyridine,
5-chloro-6-(2,4,6-trifluorophenyl)-N-[(1R)-1,2,2-trimethylpropyl][1,2,4]triazolo[1,5-a]pyrimidine-7-amine,
5-chloro-7-(4-methylpiperidin-1-yl)-6-(2,4,6-trifluorophenyl)[1,2,4]triazolo[1,5-a]pyrimidine,
5-chloro-N-[(1R)-1,2-dimethylpropyl]-6-(2,4,6-trifluorophenyl) [1,2,4]triazolo[1,5-a]pyrimidine-7-amine,
methyl 2-[[[cyclopropyl[(4-methoxyphenyl)imino]methyl]thio]methyl]-alpha-(methoxymethylene) benzacetate,
methyl 1-(2,3-dihydro-2,2-dimethyl-1H-inden-1-yl)-1H-imidazole-5-carboxylate,
N-(3',4'-dichloro-5-fluorobiphenyl-2-yl)-3-(difluoromethyl)-1-methyl-1H-pyrazole-4-carboxamide,
N-(3-ethyl-3,5,5-trimethylcyclohexyl)-3-formylamino-2-hydroxy benzamide,
N-(4-chloro-2-nitrophenyl)-N-ethyl-4-methylbenzenesulphonamide,
N-(4-chlorobenzyl)-3-[3-methoxy-4-(prop-2-yn-1-yloxy) phenyl]propanamide,
N-[(4-chlorophenyl)(cyano)methyl]-3-[3-methoxy-4-(prop-2-yn-1-yloxy)phenyl]propanamide,
N-(5-bromo-3-chloropyridin-2-yl)methyl-2,4-dichloronicotinamide,
N-[1-(5-bromo-3-chloropyridin-2-yl)ethyl]-2,4-dichloronicotinamide,
(2S)—N-[2-[4-[[3-(4-chlorophenyl)-2-propynyl]oxy]-3-methoxyphenyl]ethyl]-3-methyl-2-[(methylsulphonyl) amino]butanamide,
N-{(Z)-[(cyclopropylmethoxy)imino][6-(difluoromethoxy)-2,3-difluorophenyl]methyl}-2-benzacetamide,
N-{2-[1,1'-bi(cyclopropyl)-2-yl]phenyl}-3-(difluoromethyl)-1-methyl-1H-pyrazole-4-carboxamide,
N-{2-[3-chloro-5-(trifluoromethyl)pyridin-2-yl]ethyl}-2-(trifluoromethyl)benzamide,
N-ethyl-N-methyl-N'-{2-methyl-5-(trifluoromethyl)-4-[3-(trimethylsilyl)propoxy]phenyl}imidoformamide,
O-[1-[(4-methoxyphenoxy)methyl]-2,2-dimethylpropyl]-1H-imidazole-1-carbothioic acid,
2-amino-4-methyl-N-phenyl-5-thiazolecarboxamide,
2,4-dihydro-5-methoxy-2-methyl-4-[[[[1-[3-(trifluoromethyl)phenyl]ethylidene]amino]oxy]methyl]phenyl]-3H-1,2,4-triazol-3-one (CAS No. 185336-79-2),
N-(6-methoxy-3-pyridinyl)cyclopropane carboxamide,
Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.
Insecticides/Acaricides/Nematicides:
Acetylcholine Esterase (AChE) Inhibitors
　　Carbamates,
　　　　for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulphan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
　　Organophosphates,
　　　　for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulphotep, sulprofos, tebupirimfos, temephos, terbufos, tetrachlorvinphos, thiometon, triazophos, triclorfon, vamidothion Sodium Channel Modulators/Voltage-Dependent Sodium Channel Blockers
Pyrethroids,
for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum)
DDT
Oxadiazines,
for example indoxacarb
Semicarbazone,
for example metaflumizon (BAS3201)

Acetylcholine Receptor Agonists/Antagonists
Chloronicotinyls,
for example acetamiprid, clothianidin, dinotefuran, imidacloprid, nitenpyram, nithiazine, thiacloprid, thiamethoxam, AKD-1022, imidaclothiz
Nicotine, bensultap, cartap Acetylcholine Receptor Modulators
Spinosyns,
for example spinosad and spinetoram (XDE-175; WO 9700265 A1)

GABA-Controlled Chloride Channel Antagonists
Organochlorines,
for example camphechlor, chlordane, endosulphan, gamma-HCH, HCH, heptachlor, lindane, methoxychlor
Fiprols,
for example acetoprole, ethiprole, fipronil, pyrafluprole, pyriprole, vaniliprole Chloride Channel Activators
Mectins,
for example abamectin, emamectin, emamectin-benzoate, ivermectin, lepimectin, milbemycin Juvenile Hormone Mimetics,
for example diofenolan, epofenonane, fenoxycarb, hydroprene, kinoprene, methoprene, pyriproxifen, triprene Ecdysone Agonists/Disruptors
Diacylhydrazines,
for example chromafenozide, halofenozide, methoxyfenozide, tebufenozide Chitin Biosynthesis Inhibitors
Benzoylureas,
for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
Buprofezin
Cyromazine Oxidative Phosphorylation Inhibitors, ATP Disrupters
Diafenthiuron
Organotin compounds,
for example azocyclotin, cyhexatin, fenbutatin-oxide Oxidative Phosphorylation Decouplers Acting by Interrupting the H-Proton Gradient
Pyrroles,
for example chlorfenapyr
Dinitrophenols,
for example binapacryl, dinobuton, dinocap, DNOC, meptyldinocap Site-I Electron Transport Inhibitors
METI's,
for example fenazaquin, fenpyroximate, pyrimidifen, pyridaben, tebufenpyrad, tolfenpyrad
Hydramethylnon
Dicofol Site-II Electron Transport Inhibitors
Rotenone Site-III Electron Transport Inhibitors
Acequinocyl, fluacrypyrim Microbial Disrupters of the Insect Gut Membrane
*Bacillus thuringiensis* strains Lipid Synthesis Inhibitors
Tetronic Acids,
for example spirodiclofen, spiromesifen
Tetramic Acids,
for example spirotetramat, cis-3-(2,5-dimethylphenyl)-4-hydroxy-8-methoxy-1-azaspiro[4.5]dec-3-en-2-one Carboxamides,
for example flonicamid Octopaminergic Agonists,
for example amitraz Inhibitors of Magnesium-Stimulated ATPase,
Propargite Nereistoxin Analogues,
for example thiocyclam hydrogen oxalate, thiosultap-sodium Ryanodine Receptor Agonists,
Benzodicarboxamides,
for example flubendiamide
Anthranilamides,
for example Rynaxypyr (3-bromo-N-{4-chloro-2-methyl-6-[(methylamino)carbonyl]-phenyl}-1-(3-chloropyridin-2-yl)-1H-pyrazole-5-carboxamide)

Biologicals, Hormones or Pheromones
azadirachtin, *Bacillus* spec., *Beauveria* spec., codlemone, *Metarrhizium* spec., *Paecilomyces* spec., thuringiensin, *Verticillium* spec.

Active Compounds with Unknown or Unspecific Mechanisms of Action
Fumigants,
for example aluminium phosphide, methyl bromide, sulphuryl fluoride
Antifeedants,
for example cryolite, flonicamid, pymetrozine
Mite Growth Inhibitors,
for example clofentezine, etoxazole, hexythiazox
Amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulphluramid, tetradifon, tetrasul, triarathene, verbutin A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds combinations is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defense of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defense of the plants against fungi, bacteria and viruses by systemic acquired resistance (SAR), systemic, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis*, *Periplaneta americana*, *Blattela germanica*, *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus*, *Chlorophorus pilosis*, *Anobium punctatum*, *Xestobium rufovillosum*, *Ptilinus pectinicornis*, *Dendrobium pertinex*, *Emobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthes rugicollis*, *Xyleborus* spec. *Tryptodendron* spec. *Apate monachus*, *Bostrychus capucins*, *Heterobostrychus brunneus*, *Sinoxylon* spec. *Dinoderus minutus*;

Hymenopterons, such as *Sirex juvencus*, *Urocerus gigas*, *Urocerus gigas taignus*, *Urocerus augur*;

Termites, such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis*, *Coptotermes formosanus*;

Bristletails, such as *Lepisma saccharina*.

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, such as hulls, screens, nets, buildings, moorings and signalling systems, against fouling.

Furthermore, the compounds according to the invention, alone or in combination with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Avicularidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

PREPARATION EXAMPLES

Method 1

N-[(6-chloropyridin-3-yl)methyl]-N'-cyano-N-(2,2-difluoroethyl)ethanimidamide

Example I-1

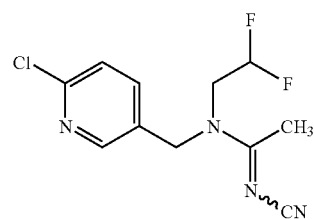

6.5 g (44.2 mmol) of N'-cyano-N-(2,2-difluoroethyl)ethanimidamide are stirred into 250 ml of acetonitrile, and 18.7 g (57.4 mmol) of cesium carbonate, 8.6 g (53.0 mmol) of 2-chloro-5-(chloromethyl)pyridine and 1.1 g (4.4 mmol) of cesium iodide are added successively. The reaction mixture is then stirred at reflux temperature for 5 hours and subsequently concentrated under reduced pressure, and the residue that remains is purified by column chromatography on silica gel using the mobile phase mixture ethyl acetate:cyclohexane (3:1). This gives 4.7 g (37% of theory) of N-[(6-chloropyridin-3-yl)methyl]-N'-cyano-N-(2,2-difluoroethyl)ethanimidamide.

$^1$H NMR (CDCl$_3$): δ [ppm]=2.52+2.53 (2 s, 3H), 3.77 (m, 2H), 4.75+4.84 (2 s, 2H), 5.97+6.14 (2 tt, 1H), 7.35+7.42 (2 d, 1H), 7.48+7.68 (2 dd, 1H), 8.26+8.30 (2 d, 1H).

$^{13}$C NMR (CDCl$_3$): δ [ppm]=19.3, 19.4, 49.8, 50.6, 50.8, 51.9, 112.5, 113.0, 115.9, 116.2, 124.7, 125.0, 136.7, 136.8, 137.0, 139.0, 147.9, 149.1, 151.6, 152.1, 173.5, 173.7.

LC-MS: m/z=273.1 (M+H$^+$, 100%)

As can be seen from the doubling of the signals in the $^1$H— and $^{13}$C NMR spectra, the N-[(6-chloropyridin-3-yl)methyl]-N'-cyano-N-(2,2-difluoroethyl)ethanimidamide is present as a mixture of E/Z isomers.

The compounds of the formula (I) listed in Table 1 below can be prepared analogously.

TABLE 1

(I)

$$A-B-N(R^1)-C(R^2)=N-CN$$

| Ex. No. | A | B | R¹ | R² | Physical data[a] |
|---|---|---|---|---|---|
| I-2 | 2-bromo-3-fluoro-5-methylpyridin-5-yl | CH₂ | CH₂CHF₂ | CH₃ | δ = 2.41 + 2.46 (2s, 3H), 3.86 (m, 2H), 4.75 + 4.78 (2s, 2H), 6.06 + 6.13 (2tt, 1H), 7.48 (m, 1H), 8.12 + 8.14 (2s, 1H); LC-MS: m/z = 335 (⁷⁹Br) and 337 (⁸¹Br) (M + H⁺, 100%). |
| I-3 | 2-chloro-3,5-difluoro-substituted phenyl | CH(CH₃) | CH₂CHF₂ | CH₃ | LC-MS: m/z = 322.0 (M + H⁺, 100%). |
| I-4 | 2-chloro-5-methylpyridin-5-yl | CH₂ | CH₂CF₃ | CH₃ | δ = 2.44 + 2.47 (2s, 3H), 4.24 (m, 2H), 4.79 (s, 2H), 7.38 (m, 1H), 7.62 (m, 1H), 8.27 (m, 1H); LC-MS: m/z = 291.0 (M + H⁺, 100%). |
| I-5 | 2-chloro-thiazol-5-yl | CH₂ | CH₂CHF₂ | CH₃ | δ = 2.39 + 2.46 (2s, 3H), 3.85 (m, 2H), 4.78 + 4.82 (2s, 2H), 6.05 + 6.11 (2tm, 1H), 7.49 + 7.55 (2s, 1H); LC-MS: m/z = 278.9 (M + H⁺, 100%). |
| I-6 | 2-chloro-5-methylpyridin-5-yl | CH₂ | CH₂CHF₂ | C₂H₅ | δ = 1.23 (m, 3H), 2.78 (m, 2H), 3.84 (m, 2H), 4.76 (s, 2H), 6.09 (m, 1H), 7.37 (m, 1H), 7.61 (m, 1H), 8.26 (s, 1H); LC-MS: m/z = 287.0 (M + H⁺, 100%). |
| I-7 | 2-chloro-3,5-difluoro-substituted phenyl | (CH)CH₃ | CH₂CHF₂ | C₂H₅ | LC-MS: m/z = 336.0 (M + H⁺, 100%). |
| I-8 | 2-trifluoromethyl-5-methylpyridin-5-yl | CH₂ | CH₂CHF₂ | CH₃ | δ = 2.41 + 2.47 (2s, 3H), 3.89 (m, 2H), 4.85 + 4.87 (2s, 2H), 6.07 + 6.15 (2tt, 1H), 7.78 (m, 2H), 8.61 (s, 1H); LC-MS: m/z = 307.0 (M + H⁺, 100%). |
| I-9 | 2,3-dichloro-5-methylpyridin-5-yl | CH₂ | CH₂CHF₂ | CH₃ | δ = 2.41 + 2.45 (2s, 3H), 3.86 (m, 2H), 4.74 + 4.77 (2s, 2H), 6.06 + 6.13 (2tt, 1H), 7.78 + 7.82 (2s, 1H), 8.20 + 8.23 (2s, 1H); LC-MS: m/z = 307.0 (M + H⁺, 100%). |
| I-10 | 2-chloro-3-methyl-5-methylpyridin-5-yl | CH₂ | CH₂CHF₂ | CH₃ | δ = 2.35 + 2.36 + 2.42 + 2.46 (4s, 6H), 3.84 (m, 2H), 4.70 + 4.75 (2s, 2H), 6.04 + 6.12 (2tt, 1H), 7.51 + 7.56 (2s, 1H), 8.08 + 8.11 (2s, 1H); LC-MS: m/z = 287.0 (M + H⁺, 100%). |

TABLE 1-continued

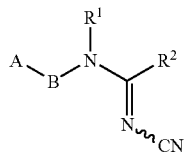

(I)

| Ex. No. | A | B | R¹ | R² | Physical data[a] |
|---|---|---|---|---|---|
| I-11 | 6-chloropyridin-3-yl | CH₂ | (CH₂)₂CF₃ | CH₃ | δ = 2.39 + 2.45 (2s, 3H), 2.55 (m, 2H), 3.67 (m, 2H), 4.66 + 4.70 (2s, 2H), 7.38 (m, 1H), 7.62 (m, 1H), 8.27 (m, 1H); LC-MS: m/z = 305.1 (M + H⁺, 100%). |
| I-12 | 6-chloropyridin-3-yl | CH₂ | CH₂CF₂CF₃ | CH₃ | δ = 2.45 (s, 3H), 4.30 (m, 2H), 4.81 (m, 2H), 7.40 (m, 1H), 7.64 (m, 1H), 8.27 (m, 1H); LC-MS: m/z = 341.0 (M + H⁺, 100%). |
| I-13 | 6-chloropyridin-3-yl | CH₂ | CH₂CH₂F | CH₃ | δ = 2.39 + 2.44 (2s, 3H), 3.77 (m, 2H), 4.58 (m, 2H), 4.73 + 4.75 (2s, 2H), 7.38 (m, 1H), 7.65 (m, 1H), 8.28 (m, 1H); LC-MS: m/z = 255.1 (M + H⁺, 100%). |
| I-14 | 6-chloropyridin-3-yl | CH₂ | CH₂CHClF | CH₃ | LC-MS: m/z = 289.1 (M + H⁺, 100%). |
| I-15 | 6-chloropyridin-3-yl | CH₂ | CH₂CF₂CH₃ | CH₃ | δ = 1.64 + 1.67 (2t, 3H), 2.42 + 2.44 (2s, 3H), 3.87 + 3.99 (2t, 2H), 4.80 (s, 2H), 7.38 (m, 1H), 7.65 (m, 1H), 8.28 (m, 1H); LC-MS: m/z = 287.1 (M + H⁺, 100%). |
| I-16 | 6-chloropyridin-3-yl | CH₂ | (CH₂)₂CF=CF₂ | CH₃ | δ = 2.39 + 2.43 (2s, 3H), 2.64 (m, 2H), 3.65 (m, 2H), 4.65 + 4.70 (2s, 2H), 7.38 (m, 1H), 7.64 (m, 1H), 8.28 (m, 1H); LC-MS: m/z = 317.1 (M + H⁺, 100%). |

[a] ¹H-NMR (CD₃CN)

Method 2
N-[(6-chloropyridin-3-yl)methyl]-N'-cyano-N-(3-fluoropropyl)ethanimidamide Example I-17

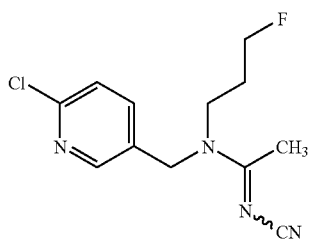

In 10 ml of methanol, 500 mg (2.47 mmol) of N-[(6-chloropyridin-3-yl)methyl]-3-fluoropropan-1-amine and 242 mg (2.47 mmol) of methyl N-cyanethanimidoacetate are stirred at room temperature for 4 days. The reaction mixture is concentrated under reduced pressure and then taken up in ethyl acetate, washed successively twice with 1 N aqueous hydrochloric acid, twice with 1 N aqueous sodium hydroxide solution and saturated sodium chloride solution and dried over sodium sulphate. Concentration of the organic phase under reduced pressure and purification of the residue by column chromatography on silica gel using the mobile phase mixture ethyl acetate:cyclohexane (1:1) gives 56 mg (8% of theory) of N-[(6-chloropyridin-3-yl)methyl]-N'-cyano-N-(3-fluoropropyl)ethanimidamide ¹H NMR (CD₃CN): δ [ppm]=2.38+2.43 (2 s, 3H), 3.54 (m, 2H), 4.47 (dm, 2H), 4.65+4.70 (2 s, 2H), 7.38 (m, 1H), 7.65 (m, 1H), 8.29 (m, 1H).

LC-MS: m/z=269.1 (M+H⁺, 100%)

Analogously, it is possible to prepare:
N-[(6-chloropyridin-3-yl)methyl]-N'-cyano-N-(2,2-difluoroethyl)ethanimidamide (for analytical data see Example I-1).

Method 3
N-[(6-chloropyridin-3-yl)methyl]N'-cyano-N-(3,3-dichloroprop-2-en-1-yl)ethanimidamide Example I-18

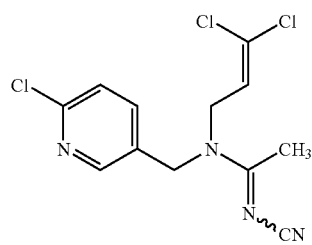

174 mg (0.83 mmol) of N-[(6-chloropyridin-3-yl)methyl]-N'-cyanoethanimidamide are stirred into 5 ml of acetonitrile, and 543 mg (1.67 mmol) of cesium carbonate, 166 mg (0.88 mmol) of 3-bromo-1,1-dichloroprop-1-ene and 22 mg (0.08 mmol) of cesium iodide are added successively. The reaction mixture is then stirred at room temperature for 1 hour. The reaction mixture is concentrated under reduced pressure and then taken up in ethyl acetate, washed successively with 1 N aqueous hydrochloric acid, 1 N aqueous sodium hydroxide solution and saturated sodium chloride solution and dried over sodium sulphate. Concentration of the organic phase under reduced pressure and purification of the residue by column chromatography on silica gel using the mobile phase mixture ethyl acetate:cyclohexane (2:1) gives 215 mg (77% of theory) of N-[(6-chloropyridin-3-yl)methyl]-N'-cyano-N-(3,3-dichloroprop-2-en-1-yl)ethanimidamide $^1$H NMR (CD$_3$CN): δ [ppm]=2.43 (s, 3H), 4.15 (m, 2H), 4.65+4.69 (2 s, 2H), 6.00 (t, 1H), 7.39 (m, 1H), 7.65 (m, 1H), 8.30 (m, 1H).

LC-MS: m/z=317.0 (M+H$^+$, 100%)
Analogously, it is possible to prepare:
N-[(6-chloropyridin-3-yl)methyl]-N'-cyano-N-(2,2-difluoroethyl)ethanimidamide (for analytical data I-1).

N-[(6-chloropyridin-3-yl)methyl]-N'-cyano-N-(3,3-difluoroprop-2-en-1-yl)ethanimidamide Example I-19

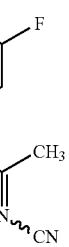

$^1$H NMR (CD$_3$CN): δ [ppm]=2.40+2.44 (2 s, 3H), 4.03 (m, 2H), 4.50 (m, 1H), 4.63+4.68 (2 s, 2H), 7.39 (m, 1H), 7.65 (m, 1H), 8.28 (m, 1H).

LC-MS: m/z=285.1 (M+H$^+$, 100%)

Preparation of the Starting Materials

Compounds of the Formula (HN(R$^1$)—C(R$^2$)=N—CN) (IV)

IV-1

N'-cyano-N-(2,2-difluoroethyl)ethanimidamide

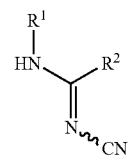

At room temperature, 8.3 g (101.9 mmol) of 2,2-difluoroethanamine and 10.0 g (101.9 mmol) of methyl N-cyanoethanimidoacetate are stirred in 100 ml of methanol for 3 hours. The reaction mixture is concentrated under reduced pressure, giving 14.7 g (98% of theory) of N'-cyano-N-(2,2-difluoroethyl)ethanimidamide.

$^1$H NMR (CD$_3$CN): δ [ppm]=2.27 (s, 3H), 3.67 (m, 2H), 5.97 (tt, 1H), 7.03 (br. s, 1H).

LC-MS: m/z=148.1 (M+H$^+$, 100%).

The compounds of the formula (IV) listed in Table 2 below can be prepared analogously.

TABLE 2

(IV)

| Ex. No. | R$^1$ | R$^2$ | Physical data$^{a)}$ |
|---|---|---|---|
| IV-2 | CH$_2$CF$_3$ | CH$_3$ | δ = 2.29 (s, 3H), 4.01 (m, 2H), 7.14 (br. s, 1H); LC-MS: m/z = 166.1 (M + H$^+$, 100%). |
| IV-3 | CH$_2$CHF$_2$ | C$_2$H$_5$ | δ = 1.24 (t, 3H), 2.59 (q, 2H), 3.66 (m, 2H), 5.97 (tt, 1H), 6.96 (br. s, 1H); LC-MS: m/z = 162.1 (M + H$^+$, 100%). |
| IV-4 | (CH$_2$)$_2$CF$_3$ | CH$_3$ | $^{b)}$ |
| IV-5 | CH$_2$CF$_2$CF$_3$ | CH$_3$ | $^{b)}$ |
| IV-6 | CH$_2$CH$_2$F | CH$_3$ | $^{b)}$ |
| IV-7 | CH$_2$CHClF | CH$_3$ | δ = 2.27 (s, 3H), 3.82 (m, 2H), 6.38 (ddd, 1H), 7.20 (br. s, 1H); LC-MS: m/z = 164.0 (M + H$^+$, 100%). |
| IV-8 | CH$_2$CF$_2$CH$_3$ | CH$_3$ | $^{b)}$ |
| IV-9 | (CH$_2$)$_2$CF=CF$_2$ | CH$_3$ | δ (DMSO-d$_6$) = 2.20 (s, 3H), 2.56 (m, 2H), 3.38 (q, 2H), 8.78 (br. s, 1H); LC-MS: m/z = 192.0 (M + H$^+$, 100%). |

$^{a)1}$H-NMR (CD$_3$CN)
$^{b)}$The crude product was (after examination by analytical HPLC) directly reacted further without further analysis.

Compounds of the Formula (A-CH$_2$-E) (V, B=CH$_2$)

Va-1

(5,6-dichloropyridin-3-yl)methanol (E=OH, A=5,6-dichloropyrid-3-yl) (R. Graf et al. *J. Prakt. Chem.* 1932, 134 177-87)

At 0° C., 859 ml (859 mmol) of a 1 M solution of boran/tetrahydrofuran complex in tetrahydrofuran are added dropwise to 110 g (573 mmol) of 5,6-dichloro-nicotinic acid in 250 ml of tetrahydrofuran. The mixture is warmed to room temperature and stirred at this temperature for 3 hours. After cooling to 0° C., the reaction mixture is made alkaline using saturated aqueous potassium carbonate solution, most of the tetrahydrofuran is removed using a rotary evaporator and the residue is extracted repeatedly with ethyl acetate. The combined organic phases are washed with water and saturated in aqueous sodium chloride solution and dried over sodium sulphate. The organic phase is concentrated under reduced pressure and the residue is purified by column chromatography on silica gel (silica gel 60-Merck, particle size: 0.04 to 0.063 mm) using the molar phase mixture ethyl acetate:cyclohexane (1:2), giving 62 g (61% of theory) of (5,6-dichloropyridin-3-yl)methanol.

$^1$H NMR (CD$_3$CN): δ [ppm]=3.31 (t, 1H), 4.60 (d, 2H), 7.85 (s, 1H), 8.26 (s, 1H)

The compound (Va-5) from Table 3 was also prepared analogously to the procedure for the compound (Va-1).

Va-2

3-bromomethyl-5,6-dichloropyridin (E=Br, A=5,6-dichloropyrid-3-yl) (cf. WO 2000046196 A1)

At 0° C., 16.40 g (62.52 mmol) of triphenylphosphine and 11.66 g (65.50 mmol) of N-bromosuccinimide are added to a solution of 10.60 g (59.55 mmol) of (5,6-dichloropyridin-3-yl)methanol (Va-1) in 100 ml of dichloromethane. After 2 h, the reaction mixture is largely concentrated and the residue is purified by column chromatography on silica gel (silica gel 60-Merck, particle size: 0.04 to 0.063 mm) using the mobile phase mixture ethyl acetate:cyclohexane (1:5). This gives 12.4 g (86% of theory) of 3-bromomethyl-5,6-dichloropyridin.

$^1$H NMR (CD$_3$CN): δ [ppm]=4.53 (s, 2H), 7.97 (s, 1H), 8.35 (s, 1H)

The compounds (Va-6) to (Va-8) from Table 3 were prepared analogously to the procedure for compound (Va-2).

Va-3

3-bromomethyl-6-chloro-5-iodopyridine (E=Br, A=6-chloro-5-iodopyrid-3-yl)

4.60 g (18.15 mmol) of 6-chloro-5-iodo-3-methylpyridine (Setliff et al., J. Chem. Engineering Data (1976), 21(2), 246-7), 3.39 g (19.06 mmol) of N-bromosuccinimide and 0.30 g (1.82 mmol) of 2,2'-azobis(2-methylpropannitrile) in 500 ml of chlorobenzene are boiled under reflux for about 16 hours. The reaction mixture is washed with saturated aqueous sodium sulphite solution and sodium bicarbonate solution and then dried over sodium sulphate and concentrated under reduced pressure. Column chromatography of the residue on silica gel (silica gel 60-Merck, particle size: 0.04 to 0.063 mm) using the mobile phase mixture ethyl acetate:cyclohexane (1:10) gives 3.86 g (38% of theory) of 3-bromomethyl-6-chloro-5-iodopyridine.

$^1$H NMR (CD$_3$CN): δ [ppm]=4.48 (s, 2H), 8.30 (s, 1H), 8.40 (s, 1H)

The compound (Va-9) from Table 3 was prepared analogously to the procedure for the compound (Va-3).

Va-4

6-chloro-3-chloromethyl-5-fluoropyridine (E=Cl, A=6-chloro-5-fluoropyrid-3-yl)

1.00 g (6.87 mmol) of 6-chloro-5-fluoro-3-methylpyridine (F. L. Setliff, Organic Preparations and Procedures International 1971, 3, 217-222), 1.01 g (7.56 mmol) of N-chlorosuccinimide and 0.11 g (0.69 mmol) of 2,2'-azobis(2-methylpropannitrile) in 100 ml of chlorobenzene are boiled under reflux for 2 days. During this reaction, after about 16 hours and 32 hours, a further 1.01 g (7.56 mmol) of N-chlorosuccinimide and 0.11 g (0.69 mmol) of 2,2'-azobis(2-methylpropannitrile) are added in each case. The reaction mixture is washed with saturated aqueous sodium sulphite solution and sodium bicarbonate solution and then dried over sodium sulphite and concentrated under reduced pressure. Column chromatography of the residue on silica gel (silica gel 60-Merck, particle size: 0.04 to 0.063 mm) using the mobile phase mixture ethyl acetate:cyclohexane (1:20) gives 0.65 g (53% of theory) of 6-chloro-3-chloromethyl-5-fluoropyridine.

$^1$H NMR (CD$_3$CN): δ [ppm]=4.68 (s, 2H), 7.69 (d, 1H), 8.27 (s, 1H)

Further compounds (Va-5) to (Va-10) of the formula (Va) are listed in Table 3 below.

TABLE 3

| | E—CH$_2$—A (Va) | | |
|---|---|---|---|
| Ex. No. | E | A | Physical data[a)] |
| Va-5 | OH | ![structure: 3-Cl, 2-Br, 5-methylpyridine] | 3.30 (t, 1H), 4.59 (d, 2H), 7.83 (s, 1H), 8.26 (s, 1H) |
| Va-6 | Br | ![structure: 3-CH$_3$, 2-Cl, 5-methylpyridine] | 2.37 (s, 3H), 4.52 (s, 2H), 7.70 (s, 1H), 8.24 (s, 1H) |

TABLE 3-continued

E—CH$_2$—A (Va)

| Ex. No. | E | A | Physical data[a] |
|---|---|---|---|
| Va-7 | Br | 3-Br, 2-Cl-pyridin-5-yl | 4.52 (s, 2H), 8.10 (s, 1H), 8.38 (s, 1H) |
| Va-8 | Br | 3-Cl, 2-Br-pyridin-5-yl | 4.52 (d, 2H), 7.92 (s, 1H), 8.35 (s, 1H) |
| Va-9 | Br | 3-Br, 2-Br-pyridin-5-yl | 4.50 (s, 2H), 8.07 (s, 1H), 8.37 (s, 1H) |
| Va-10 | Br | 3-F, 2-Br-pyridin-5-yl | 4.55 (s, 2H), 7.65 (d, 1H), 8.27 (s, 1H) |

[a] $^1$H-NMR (CD$_3$CN), δ [ppm]

Compounds of the Formula (A-B—N(R$^1$)H) (VI)

VI-1

N-[(6-chloro-5-fluoropyridin-3-yl)methyl]-2,2-difluoroethylamine

At 45° C., 520 mg (2.89 mmol) of 6-chloro-3-chloromethyl-5-fluoropyridine (Va-4), 1.05 ml (14.44 mmol) of 2,2-difluoroethylamine and 400 μl (2.89 mmol) of triethylamine in 50 ml of acetonitrile are stirred for about 48 hours. During the reaction, after about 16 hours and 32 hours, a further 0.42 ml (5.78 mmol) of 2,2-difluoroethylamine are added in each case. The reaction mixture is concentrated under reduced pressure and then taken up in 1 N aqueous hydrochloric acid and washed with ethyl acetate. The aqueous phase is made alkaline using 2.5 N aqueous sodium hydroxide solution and extracted repeatedly with ethyl acetate. Drying of the combined organic phases over sodium sulphate and concentration under reduced pressure gives 370 mg (57% of theory) of N-[(6-chloro-5-fluoropyridin-3-yl)methyl]-2,2-difluoroethylamine.

$^1$H NMR (CD$_3$CN): δ [ppm]=2.95 (td, 2H), 3.87 (s, 2H), 5.87 (tt, 1H), 7.62 (d, 1H), 8.17 (s, 1H).

The Following Compounds can be Prepared Analogously:

VI-2

N-[(6-chloropyridin-3-yl)methyl]-2,2-difluoroethan-1-amine $^1$H NMR (CD$_3$CN, δ, ppm)=2.93 (td, 2H), 3.80 (s, 2H), 5.85 (tt, 1H), 7.33 (d, 1H), 7.71 (dd, 1H), 8.30 (d, 1H).

VI-3

N-[(6-chloropyridin-3-yl)methyl]-3-fluoropropan-1-amine

LCMS (m/z, %)=203 (MH$^+$, 100).

VI-4

N-[(6-chloropyridin-3-yl)methyl]-2-chloro-2-fluoroethane-1-amine

LCMS (m/z, %)=223 (MH$^+$, 100).

Compounds of the Formula (A-B—NH—C(R$^2$)=N—CN) (IX)

IX-1

N-[(6-chloropyridin-3-yl)methyl]-N'-cyanoethanimidamide (cf. WO 9104965 A1)

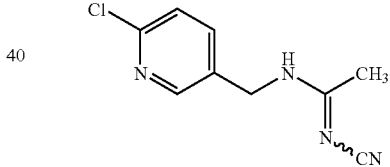

At room temperature, 500 mg (3.51 mmol) of 1-(6-chloropyridin-3-yl)methanamine and 378 mg (3.86 mmol) of methyl N-cyanoethanimidoacetate in 10 ml of methanol are stirred for 3 hours. The reaction mixture is concentrated under reduced pressure and the residue is purified by recrystallization from ethyl acetate/cyclohexane, giving 532 mg (52% of theory) of N-[(6-cyloropyridin-3-yl)methyl]-N'-cyanoethanimidamide LC-MS: m/z=209.0 (M+H$^+$, 100%).

BIOLOGICAL EXAMPLES

Example No. 1

*Myzus* Test (Spray Treatment)

| Solvents: | 78.0 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*), which are infested by all stages of the green peach aphid (*Myzus persicae*) are sprayed with an active compound preparation of the desired concentration.

After the desired period of time, the activity in % is determined. 100% means that all aphids have been killed, 0% means that none of the aphids have been killed.

In this test, for example, the following compounds of the Preparation Examples show an activity of ≧80% at an application rate of 500 g/ha:
Ex. No. I-2, I-5, I-6, I-8, I-9, I-10, I-11, I-12, I-14, I-15, I-16, I-17, I-19, I-18

Example No. 2

*Meloidogyne* Test (Spray Treatment)

Solvent: 80 parts by weight of acetone

To produce a suitable preparation of active compound, 1 part by weight of active compound is mixed with the stated amounts of solvent, and the concentrate is diluted with water to the desired concentration.

Containers are filled with sand, solution of active compound, *Meloidogyne incognita* egg/larvae suspension and lettuce seeds. The lettuce seeds germinate and the plants develop. On the roots, galls are formed.

After the desired period of time, the nematicidal activity is determined in % by the formation of galls. 100% means that no galls were found; 0% means that the number of galls on the treated plants corresponds to that of the untreated control.

In this test, for example, the following compounds of the Preparation Examples show an activity of ≧80% at an application rate of 20 ppm:
Ex. No. I-3

Example No. 3

*Phaedon* Test (Spray Treatment)

| Solvents: | 78.0 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) are sprayed with an active compound preparation of the desired concentration and, after drying, populated with larvae of the mustard beetle (*Phaedon Cochleariae*)

After the desired period of time, the activity in % is determined. 100% means that all beetle larvae have been killed, 0% means that none of the beetle larvae have been killed.

In this test, for example, the following compounds of the Preparation Examples show an activity of ≧80% at an application rate of 500 g/ha:
Ex. No. I-2, I-9, I-10, I-19

Example No. 4

*Bemisia Tabaci* (Spray Treatment)

| Solvents: | 78.0 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of cotton leaves (*Gossypium hirsutum*) which are infested by larvae of the white fly (*Bemisia tabaci*) are sprayed with an active compound preparation of the desired concentration.

After the desired period of time, the activity in % is determined. 100% means that all white flies have been killed, 0% means that none of the white flies have been killed.

In this test, for example, the following compounds of the Preparation Examples show an activity of ≧80% at an application rate of 500 g/ha:
Ex. No. I-2

Example No. 5

*Lucilia Cuprina* Test

Solvent: dimethyl sulphoxide

To produce a suitable preparation of active compound, 1 part by weight of active compound is mixed with the stated amount of water and the concentrate is diluted with water to the desired concentration.

Containers containing horsemeat treated with the active compound preparation of the desired concentration are populated with *Lucilia cuprina* larvae.

After the desired period of time, the kill in % is determined. 100% means that all larvae have been killed; 0% means that none of the larvae have been killed.

In this test, for example, the following compounds of the Preparation Examples show an activity of ≧80% at an application rate of 100 ppm:
Ex. No. I-2

COMPARATIVE EXAMPLES

Example No. 1

*Phaedon* Test (Spray Treatment)

| Solvents: | 78.0 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) are sprayed with an active compound preparation of the desired concentration and, after drying, populated with larvae of the mustard beetle (*Phaedon cochleariae*)

After the desired period of time, the activity in % is determined. 100% means that all beetle larvae have been killed, 0% means that none of the beetle larvae have been killed.

Results are shown in the table further below.

Example No. 2

*Ctenocephalides Felis*; Oral

Solvent: Dimethyl sulphoxide

To produce a suitable preparation of active compound, 1 part by weight of active compound is mixed with the stated amount of water. Part of the concentrate is diluted with citrated cattle blood, and the desired concentration is prepared.

20 unfed adult fleas (*Ctenocephalides felis*) are placed into a chamber whose top and bottom ends are closed with gauze. A metal cylinder whose bottom end is closed with parafilm is placed onto the chamber. The cylinder contains the blood/active compound preparation, which can be taken up by the fleas through the parafilm membrane. The blood is warmed to 37° C., but the flea chamber is at room temperature.

After the desired period of time, the kill in % is determined. 100% means that all fleas have been killed; 0% means that none of the fleas have been killed.

The results are shown in the table further below.

Example No. 3

*Musca Domestica* Test

Solvent: Dimethyl sulphoxide

To produce a suitable preparation of active compound, 1 part by weight of active compound is mixed with the stated amount of water, and the concentrate is diluted with water to the desired concentration.

Containers containing a sponge treated with the active compound preparation of the desired concentration are populated with adult *Musca domestica*.

After the desired period of time, the kill in % is determined. 100% means that all flies have been killed; 0% means that none of the flies have been killed.

The results are shown in the table below (d=days).

in which

A represents 6-chloropyrid-3-yl, 6-bromopyrid-3-yl, 6-methylpyrid-3-yl, 6-trifluoromethyl-pyrid-3-yl, 2-methylpyrimidin-5-yl, 2-chloropyrimid-5-yl, 1H-pyrazol-4-yl which is optionally substituted in the 1-position by methyl or ethyl and in the 3-position by chlorine, 1H-pyrazol-5-yl, 3-methylpyrazol-5-yl, 2-bromo-1,3-thiazol-5-yl, 2-chloro-1,3-thiazol-5-yl, isoxazol-5-yl which is optionally substituted in the 3-position by methyl, ethyl, chlorine, or bromine, 3-methyl-1,2,4-oxadiazol-5-yl, 1-methyl-1,2,4-triazol-3-yl, or 1,2,5-thiadiazol-3-yl, or A represents 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl or 5-methyl-6-bromopyrid-3-yl, or A represents a radical

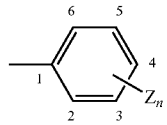

in which n represents 2 or 3, and

Z represents fluorine or chlorine, $R^1$ represents 2,2-difluoroethyl, $R^2$ represents methyl or ethyl, and B represents a radical selected from the group consisting of (B-1) to (B-9)

| Active compound Ex. No. | 1. Phaedon test spray treatment | | 2. *Ctenocephalides felis* | | 3. *Musca domestica* | |
|---|---|---|---|---|---|---|
| | g/ha | % 7 d | ppm | % 2 d | ppm | % 2 d |
| I-1 | 20 | 100 | 100 | 70 | 100 | 100 |
| I-6 | | | | | 100 | 50 |
| 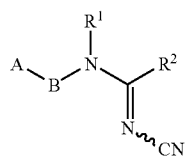 known from WO 91/04965 | 20 | 0 | 100 | 30 | 100 | 0 |

The invention claimed is:

1. A compound of the formula (I)

 B-1

 B-2

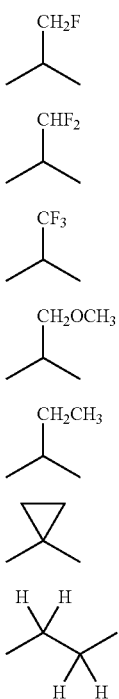

B-3

B-4

B-5

B-6

B-7

B-8

B-9

2. The compound according to claim 1 in which

A represents a radical selected from the group consisting of 6-chloropyrid-3-yl, 6-bromopyrid-3-yl, 2-methylpyrimidin-5-yl, 2-chloropyrimid-5-yl, 3-methylisoxazol-5-yl, 3-bromoisoxazol-5-yl, 5-fluoro-6-chloropyrid-3-yl, 5,6-dichloropyrid-3-yl, 5-fluoro-6-bromopyrid-3-yl, and 2-chloro-1,3-thiazol-5-yl, $R^1$ represents 2,2-difluoroethyl, $R^2$ represents methyl, and B represents methylene (—CH$_2$—).

3. A process for preparing a compound of the formula (I) according to claim 1, comprising a) reacting in a first reaction step, a compound of the formula (II)

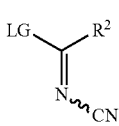

(II)

in which $R^2$ is defined in claim 1 and LG represents a suitable leaving group, with a compound of the formula (III)

R$^1$—NH$_2$ (III)

in which $R^1$ is as defined in claim 1, optionally in the presence of a suitable diluent and optionally in the presence of a basic auxiliary, to give a compound of the formula (IV)

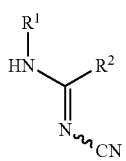

(IV)

in which $R^1$ and $R^2$ are as defined in claim 1, and then reacting in a second reaction step, a compound of formula (IV) with a compound of the formula (V)

A-B-E (V)

in which

A and B are as defined in claim 1, and

E represents a suitable leaving group LG, optionally in the presence of a suitable diluent and optionally in the presence of a basic auxiliary, or b) reacting a compound of the formula (II)

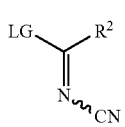

(II)

in which $R^2$ is as defined in claim 1 and LG is as defined above, with a compound of the formula (VI)

A-B-N(R$^1$)H (VI)

in which

A, B and $R^1$ are as defined in claim 1, optionally in the presence of a suitable diluent and optionally in the presence of a basic auxiliary, or c) reacting in a first reaction step an orthoester of the formula (VII)

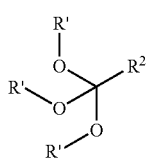

(VII)

in which $R^2$ is as defined in claim 1, and

R' represents methyl or ethyl, in situ with cyanamide, optionally in the presence of one or more diluents, to give a compound of the formula (II)

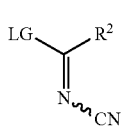

(II)

in which $R^2$ is as defined in claim 1 and LG is as defined above, and then, reacting in a second reaction step, a compound of the formula (II) with a compound of the formula (VIII)

A-B—NH$_2$ (VIII)

in which

A and B are as defined in claim 1, optionally in the presence of a suitable diluent and optionally in the presence of a basic auxiliary, to give a compound of the formula (IX)

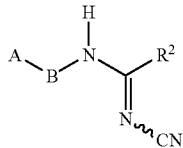

(IX)

in which

A, B, $R^2$ are as defined above, and then, reacting in a third reaction step, a compound of the formula (IX) with a compound of the formula (X)

$R^1$-E     (X)

in which $R^1$ is as defined in claim 1 and E is as defined above, optionally in the presence of a suitable diluent and optionally in the presence of a basic auxiliary.

4. A composition, comprising at least one compound of the formula (I) according to claim 1 and one or more extenders, surfactants, or combinations thereof.

5. A method for controlling pests, comprising contacting a compound of the formula (I) according to claim 1 with pests or their habitat.

6. A method for controlling pests, comprising contacting a composition according to claim 4 with pests or their habit.

7. A compound of formula (IV-1):

IV-1

8. The compound according to claim 1, having the formula:

* * * * *